(12) United States Patent
Ishii et al.

(10) Patent No.: US 10,159,448 B2
(45) Date of Patent: Dec. 25, 2018

(54) X-RAY CT APPARATUS, MEDICAL INFORMATION PROCESSING APPARATUS, AND MEDICAL INFORMATION PROCESSING METHOD

(71) Applicant: Toshiba Medical Systems Corporation, Otawara-shi (JP)

(72) Inventors: Hideaki Ishii, Nasushiobara (JP); Takuya Sakaguchi, Utsunommiya (JP); Kazumasa Arakita, Nasushiobaba (JP)

(73) Assignee: Toshiba Medical Systems Corporation, Otawara-shi (JP)

(*) Notice: Subject to any disclaimer, the term of this patent is extended or adjusted under 35 U.S.C. 154(b) by 24 days.

(21) Appl. No.: 15/613,475

(22) Filed: Jun. 5, 2017

(65) Prior Publication Data
US 2017/0347975 A1   Dec. 7, 2017

(30) Foreign Application Priority Data

Jun. 6, 2016  (JP) ................... 2016-112947
May 16, 2017 (JP) ................... 2017-097431

(51) Int. Cl.
*G06K 9/00* (2006.01)
*A61B 6/03* (2006.01)
(Continued)

(52) U.S. Cl.
CPC .............. *A61B 6/032* (2013.01); *A61B 6/463* (2013.01); *A61B 6/503* (2013.01); *A61B 6/5217* (2013.01); *A61B 5/026* (2013.01); *A61B 5/02007* (2013.01); *A61B 5/7282* (2013.01); *A61B 5/743* (2013.01); *A61B 6/488* (2013.01); *A61B 6/507* (2013.01);
(Continued)

(58) Field of Classification Search
CPC ......... A61B 5/7282; A61B 8/06; A61B 6/032; A61B 6/463; A61B 6/503; A61B 6/5217; A61B 5/743; A61B 6/507; A61B 5/02007; A61B 8/0891; A61B 6/488;
(Continued)

(56) References Cited

U.S. PATENT DOCUMENTS

| 8,909,321 B2 | 12/2014 | Sugiura |
| 2014/0334708 A1 | 11/2014 | Sakata et al. |

(Continued)

FOREIGN PATENT DOCUMENTS

| JP | 2014-87635 | 5/2014 |
| JP | 2014-108208 | 6/2014 |
| JP | 2015-110155 | 6/2015 |

*Primary Examiner* — Gregory F Cunningham
(74) *Attorney, Agent, or Firm* — Oblon, McClelland, Maier & Neustadt, L.L.P.

(57) ABSTRACT

An X-ray CT apparatus according to an embodiment includes processing circuitry. The processing circuitry collects pieces of image data in a plurality of time phases that contain at least a part of a coronary artery of a heart. The processing circuitry acquires image indexes regarding the pieces of image data. The processing circuitry extracts a set of image data from combinations of pieces of image data having a larger time interval than a predetermined time interval, of the pieces of image data, based on the image indexes in the respective pieces of image data. The processing circuitry performs fluid analysis regarding the coronary artery based on the extracted set of image data to obtain a fluid parameter regarding the coronary artery.

18 Claims, 12 Drawing Sheets

(51) Int. Cl.
*A61B 6/00* (2006.01)
*A61B 5/00* (2006.01)
*A61B 5/02* (2006.01)
*A61B 8/08* (2006.01)
*A61B 8/06* (2006.01)
*A61B 5/026* (2006.01)

(52) U.S. Cl.
CPC ............... *A61B 8/06* (2013.01); *A61B 8/0883* (2013.01); *A61B 8/0891* (2013.01); *A61B 2576/00* (2013.01); *A61M 2205/3331* (2013.01)

(58) Field of Classification Search
CPC ... A61B 2576/00; A61B 8/0883; A61B 5/026; A61M 2205/3331
USPC ........................................................ 382/104
See application file for complete search history.

(56) References Cited

U.S. PATENT DOCUMENTS

2015/0257655 A1 9/2015 Ishii et al.
2015/0335304 A1* 11/2015 Lavi ...................... G06F 19/321
 600/407
2017/0347973 A1* 12/2017 Ishii ...................... A61B 6/5235

* cited by examiner

X-RAY CT APPARATUS, MEDICAL INFORMATION PROCESSING APPARATUS, AND MEDICAL INFORMATION PROCESSING METHOD

CROSS-REFERENCE TO RELATED APPLICATIONS

This application is based on and claims the benefit of priority from Japanese Patent Application No. 2016-112947, filed on Jun. 6, 2016, and Japanese Patent Application No. 2017-97431, filed on May 16, 2017; the entire contents of which are incorporated herein by reference.

FIELD

Embodiments described herein relate generally to an X-ray CT apparatus, a medical information processing apparatus, and a medical information processing method.

BACKGROUND

Conventionally, it has been known that causes of an ischemic disease of internal organs are generally categorized as hematogenous disorder and dysfunction of the organ itself. For example, stenosis being an example of hematogenous disorder of a coronary artery is a serious lesion leading to the ischemic heart disease. With respect to the ischemic heart disease, it is required to judge whether to perform medication or stent therapy. In recent years, a method of measuring myocardial fractional flow reserve (FFR) by using a pressure wire has been recommended in a coronary angiography by a catheter as a diagnosis for performing hematogenous ischemia estimation of a coronary artery.

Meanwhile, there has been known a method of performing the hematogenous ischemia estimation of a coronary artery non-invasively by using medical images of a heart collected by a medical-diagnostic imaging apparatus such as an X-ray CT (Computed Tomography) apparatus, an MRI (Magnetic Resonance Imaging) apparatus, or an ultrasonic diagnostic apparatus. In recent years, the hematogenous ischemia estimation has been performed by such various methods, and medical treatment according to the estimation is performed.

DETAILED DESCRIPTION

According to an embodiment, an X-ray CT apparatus includes processing circuitry. The processing circuitry is configured to collect pieces of image data in a plurality of time phases that contain at least a part of a coronary artery of a heart. The processing circuitry is configured to acquire image indexes regarding a plurality of pieces of the image data. The processing circuitry is configured to extract a set of image data from combinations of pieces of image data having a larger time interval than a predetermined time interval, of the pieces of image data, based on the image indexes in the respective pieces of image data. The processing circuitry is configured to perform fluid analysis regarding the coronary artery based on the extracted set of image data to obtain a fluid parameter regarding the coronary artery.

Embodiments of an X-ray CT apparatus, a medical information processing apparatus, and a medical information processing method according to the present application will be described below in detail with reference to the accompanying drawings. The X-ray CT apparatus, the medical information processing apparatus, and the medical information processing method according to the present application are not limited to the embodiments.

First Embodiment

A first embodiment is described first. In the first embodiment, an example in which a technique disclosed in the present application is applied to an X-ray CT apparatus is described. Hereinafter, a medical information processing system including the X-ray CT apparatus is described by an example. Further, as an example, a case in which a blood vessel in a heart is set as an analysis target is described.

Figure 1:
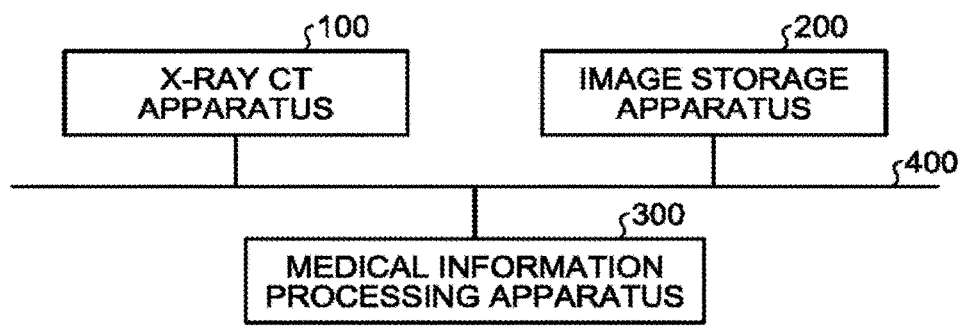
FIG. 1 is a diagram illustrating an example of a configuration of a medical information processing system according to a first embodiment.

FIG. 1 is a diagram illustrating an example of a configuration of the medical information processing system according to the first embodiment. As illustrated in FIG. 1, the medical information processing system according to the first embodiment includes an X-ray CT (Computed Tomography) apparatus 100, an image storage apparatus 200, and a medical information processing apparatus 300.

For example, the X-ray CT apparatus 100 according to the first embodiment is connected to the image storage apparatus 200 and the medical information processing apparatus 300 via a network 400, as illustrated in FIG. 1. The medical information processing system can be also connected to other medical-diagnostic imaging apparatuses such as an MRI apparatus, an ultrasonic diagnostic apparatus, and a PET (Positron Emission Tomography) apparatus via the network 400.

The image storage apparatus 200 stores therein pieces of image data collected by various kinds of medical-diagnostic imaging apparatuses. For example, the image storage apparatus 200 is realized by a computer appliance such as a server device. In the first embodiment, the image storage apparatus 200 acquires CT image data (volume data) from the X-ray CT apparatus 100 via the network 400 and memorizes the acquired CT image data in memory circuitry provided inside or outside the device.

The medical information processing apparatus 300 acquires image data from various medical-diagnostic imaging apparatuses via the network 400 and processes the acquired image data. For example, the medical information processing apparatus 300 is realized by a computer appliance such as a workstation. In the first embodiment, the medical information processing apparatus 300 acquires CT image data from the X-ray CT apparatus 100 or the image storage apparatus 200 via the network 400, and performs various types of image processing on the acquired CT image data. The medical information processing apparatus 300 displays the CT image data before performing the image processing or after performing the image processing on a display or the like.

Figure 2:
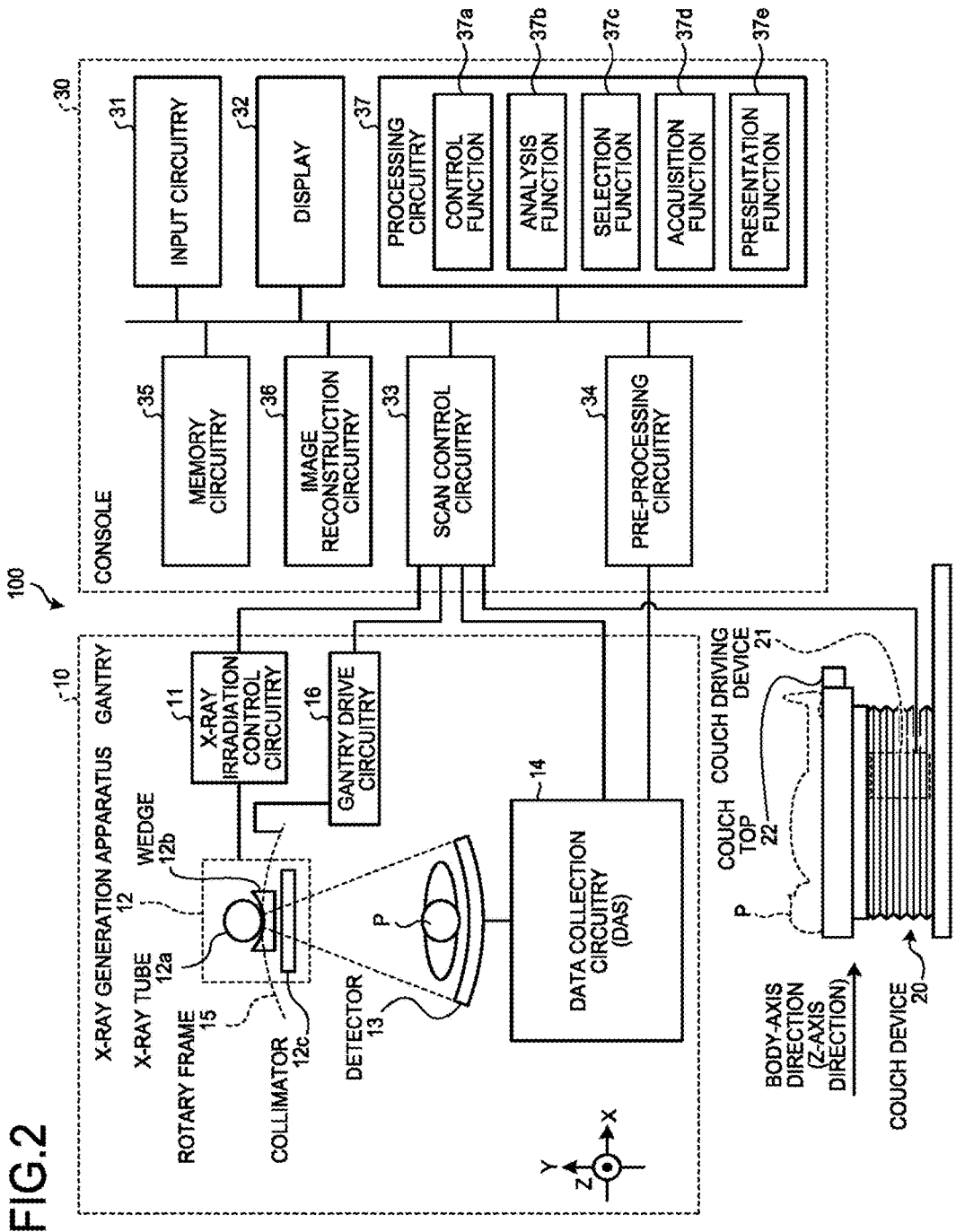
FIG. 2 is a diagram illustrating an example of a configuration of an X-ray CT apparatus according to the first embodiment.

The X-ray CT apparatus 100 collects pieces of CT image data of a subject. Specifically, the X-ray CT apparatus 100 causes an X-ray tube and an X-ray detector to revolve substantially around the subject to detect X rays having penetrated through the subject and collect projection data. The X-ray CT apparatus 100 generates time-series three-dimensional CT image data based on the collected pieces of projection data. FIG. 2 is a diagram illustrating an example of a configuration of the X-ray CT apparatus 100 according to the first embodiment. As illustrated in FIG. 2, the X-ray CT apparatus 100 according to the first embodiment includes a gantry 10, a couch device 20, and a console 30.

The gantry 10 is an apparatus that irradiates X rays to a subject P (patient) and detects X rays having penetrated through the subject. P to output detected X rays to the console 30. The gantry 10 includes X-ray irradiation control circuitry 11, an X-ray generation apparatus 12, a detector 13, data collection circuitry (DAS: Data Acquisition System) 14, a rotary frame 15, and gantry drive circuitry 16.

The rotary frame 15 is an annular frame that supports the X-ray generation apparatus 12 and the detector 13 facing each other while having the subject P therebetween, and is rotated at a high speed on a circular path centering on the subject P by the gantry drive circuitry 16 described later.

The X-ray irradiation control circuitry 11 is a device that supplies a high voltage to an X-ray tube 12a as a high-voltage generation unit, and the X-ray tube 12a generates X rays by using the high voltage supplied from the X-ray irradiation control circuitry 11. The X-ray irradiation control circuitry 11 adjusts an X-ray dosage irradiated to the subject P by adjusting a tube voltage and a tube current to be supplied to the X-ray tube 12a under control of a scan control circuitry 33 described later.

The X-ray irradiation control circuitry 11 also performs switching of a wedge 12b. The X-ray irradiation control circuitry 11 adjusts an aperture of a collimator 12c to adjust an irradiation range (a fan angle and a cone angle) of X rays. The first embodiment can be applied to a case where a plurality of types of wedges are switched manually by an operator.

The X-ray generation apparatus 12 is an apparatus that generates X rays and irradiates the generated X rays to the subject P, and includes the X-ray tube 12a, the wedge 12b, and the collimator 12c.

The X-ray tube 12a is a vacuum tube that irradiates X-ray beams to the subject P by a high voltage supplied from a high-voltage generation unit (not illustrated), and irradiates the X-ray beams to the subject P with the rotation of the rotary frame 15. The X-ray tube 12a generates X-ray beams expanding with a fan angle and a cone angle. For example, the X-ray tube 12a can expose X-rays continuously all around the subject P for full reconstruction, or in an exposure range capable of performing half reconstruction (180°+ fan angle) under control of the X-ray irradiation control circuitry 11. Further, the X-ray tube 12a can expose X rays (pulse X rays) intermittently at a preset position (a tube position) under control of the X-ray irradiation control circuitry 11. The X-ray irradiation control circuitry 11 can modulate the intensity of X rays exposed from the X-ray tube 12a. For example, the X-ray irradiation control circuitry 11 increases the intensity of X rays exposed from the X-ray tube 12a at a specific tube position, and decreases the intensity of X rays exposed from the X-ray tube 12a in a range other than the specific tube position.

The wedge 12b is an X-ray filter for adjusting the X-ray dosage of X rays emitted from the X-ray tube 12a. Specifically, the wedge 12b is a filter that passes and attenuates X rays exposed from the X-ray tube 12a so that X rays irradiated from the X-ray tube 12a to the subject P has predetermined distribution. For example, the wedge 12b is a filter obtained by processing aluminum to have a predetermined target angle and a predetermined thickness. The wedge is also referred to as "wedge filter" or "bow-tie filter".

The collimator 12c is a slit for narrowing down the irradiation range of X rays with the X-ray dosage being adjusted by the wedge 12b under control of the X-ray irradiation control circuitry 11 described later.

The gantry drive circuitry 16 revolves the X-ray generation apparatus 12 and the detector 13 on a circular path centering on the subject P by rotating the rotary frame 15.

The detector 13 is a two-dimensional array detector (a plane detector) that detects X rays having penetrated through the subject P, in which a plurality of detection element arrays obtained by arranging X-ray detection elements for a plurality of channels are arranged along a body axis direction of the subject P (a Z-axis direction in FIG. 2). Specifically, the detector 13 in the first embodiment includes X-ray detection elements arranged in multiple columns such as 320 columns along the body axis direction of the subject P, and can detect X rays having penetrated through the subject P in a wide range, for example, a range including the lungs and heart of the subject P.

The data collection circuitry 14 is a DAS and collects projection data from the detection data of X rays detected by the detector 13. For example, the data collection circuitry 14 performs amplification processing, A/D conversion processing, sensitivity correction processing between channels, and the like on X-ray intensity distribution data detected by the detector 13 to generate projection data, and transmits the generated projection data to the console 30 described later. For example, when X rays are being exposed continuously from the X-ray tube 12a during rotation of the rotary frame 15, the data collection circuitry 14 collects projection data groups for the entire circumference (for 360 degrees). The data collection circuitry 14 associates a tube position with each of the collected projection data, and transmits the data to the console 30 described later. The tube position is information indicating a projection direction of the projection data. The sensitivity correction processing between channels can be performed by a pre-processing circuitry 34 described later.

The couch device 20 is a device on which the subject P is laid, and as illustrated in FIG. 2, includes a couch driving device 21 and a couch top 22. The couch driving device 21 moves the couch top 22 in the 2-axis direction to move the subject P into the rotary frame 15. The couch top 22 is a board on which the subject P is laid.

For example, the gantry 10 causes the rotary frame 15 to rotate while moving the couch top 22, to perform helical scan by which the subject P is scanned spirally. Alternatively, the gantry 10 causes the rotary frame 15 to rotate, while the position of the subject P is fixed after having shifted the couch top 22, to perform conventional scan by which the subject P is scanned on a circular path. Alternatively, the gantry 10 executes a step-and-shoot method in which the position of the couch top 22 is shifted at a regular interval to perform the conventional scan in a plurality of scan areas.

The console 30 is a device that receives an operation on the X-ray CT apparatus 100 by an operator and reconstructs CT image data (volume data) by using projection data collected by the gantry 10. The console 30 includes, as illustrated in FIG. 2, an input circuitry 31, a display 32, the scan control circuitry 33, the pre-processing circuitry 34, a memory circuitry 35, image reconstruction circuitry 36, and processing circuitry 37.

The input circuitry 31 includes a mouse, a keyboard, a trackball, a switch, a button, a joystick, or the like used for input of various instructions and various settings by an operator of the X-ray CT apparatus 100, and transfers instructions and setting information received from the operator to the processing circuitry 37. For example, the input circuitry 31 receives shooting conditions of CT image data, reconstruction conditions at the time of reconstructing the CT image data, and image processing conditions and the like with respect to the CT image data. The input circuitry 31 also receives an operation for selecting an examination with respect to the subject P. The input circuitry 31 further receives a designation operation for designating a portion on an image.

The display 32 is a monitor referred to by an operator, and displays image data generated from CT image data to the operator, or displays a GUI (Graphical User Interface) for receiving various instructions and various settings from the operator via the input circuitry 31, under control of the processing circuitry 37. The display 32 also displays a planning screen of a scan plan and a screen during the scan.

The scan control circuitry 33 controls the behavior of the X-ray irradiation control circuitry 11, the gantry drive circuitry 16, the data collection circuitry 14, and the couch driving device 21 under control of the processing circuitry 37, to control the collection processing of projection data in the gantry 10. Specifically, the scan control circuitry 33 controls collection processing of projection data respectively in shooting for collecting positioning images (scanogram images) and main shooting (scanning) for collecting images to be used for diagnosis.

The pre-processing circuitry 34 performs logarithmic conversion processing, and correction processing such as offset correction, sensitivity correction, and beam hardening correction with respect to the projection data generated by the data collection circuitry 14, to generate corrected projection data. Specifically, the pre-processing circuitry 34 generates corrected projection data for each of pieces of projection data of positioning images generated by the data collection circuitry 14 and projection data collected by the main shooting, and stores the corrected pieces of projection data in the memory circuitry 35.

The memory circuitry 35 memorizes therein the projection data generated by the pre-processing circuitry 34. Specifically, the memory circuitry 35 memorizes therein the pieces of projection data of positioning images and projection data for diagnosis collected by the main shooting, generated by the pre-processing circuitry 34. The memory circuitry 35 also memorizes therein CT image data and the like reconstructed by the image reconstruction circuitry 36 described later. The memory circuitry 35 appropriately memorizes therein processing results by the processing circuitry 37 described later.

The image reconstruction circuitry 36 reconstructs the CT image data by using the projection data memorized in the memory circuitry 35. Specifically, the image reconstruction circuitry 36 reconstructs the CT image data respectively from the pieces of projection data of the positioning images and projection data of the images used for diagnosis. As a reconstruction method, various methods can be used such as back projection processing. Further, as the back projection processing, back projection processing by an FBP (Filtered Back Projection) method can be exemplified. Alternatively, the image reconstruction circuitry 36 can reconstruct the CT image data by using successive approximation.

The image reconstruction circuitry 36 performs various types of image processing with respect to the CT image data to generate image data. The image reconstruction circuitry 36 stores reconstructed CT image data and image data generated by various types of image processing in the memory circuitry 35.

The processing circuitry 37 controls the behavior of the gantry 10, the couch device 20, and the console 30 to execute entire control on the X-ray CT apparatus 100. Specifically, the processing circuitry 37 controls the scan control circuitry 33 to control CT scan performed on the gantry 10. The processing circuitry 37 also controls the image reconstruction circuitry 36 to control image reconstruction processing and image generation processing in the console 30. The processing circuitry 37 controls to display various types of image data to be memorized in the memory circuitry 35 on the display 32.

Due to this configuration, the X-ray CT apparatus 100 according to the first embodiment enables easy selection of appropriate data. Specifically, the X-ray CT apparatus 100 enables easy selection of appropriate data as data at the time of calculating an index value regarding blood flow by fluid analysis using medical images including blood vessels (for example, three-dimensional CT image data). For example, the X-ray CT apparatus 100 selects CT image data in an appropriate time phase as data to be used for fluid analysis from CT image data in a plurality of time phases collected over time.

As an index value regarding the blood flow, for example, there are a myocardial fractional flow reserve (FFR), a mechanical index in blood vessels, and an index regarding a flow rate of blood. The FFR is a ratio between pressure in proximal portions close to the heart and pressure in distal portions away from the heart in the blood vessels, and is expressed by, for example, "FFR=Pd (pressure in distal portions)/Pa (pressure in proximal portions)". For example, when stenosis has occurred in a blood vessel (portion to he treated), because the pressure in distal portions decreases due to stenosis, the FFR value decreases. The fluid analysis is used for judging whether to perform medical treatment by calculating the FFR value. As the mechanical index in the blood vessels, for example, there are a pressure, a vector, and shear stress. Further, the index regarding the flow rate of blood includes a flow volume and a flow rate.

Hereinafter, in the first embodiment, a case where appropriate CT image data is selected at the time of performing fluid analysis with respect to a coronary artery is described as an example. The processing circuitry 37 according to the first embodiment executes a control function 37a, an analysis function 37b, a selection function 37c, an acquisition function 37d, and a presentation function 37e as illustrated in FIG. 2. For example, respective processing functions executed by the control function 37a, the analysis function 37b, the selection function 37c, the acquisition function 37d, and the presentation function 37e being constituent elements of the processing circuitry 37 illustrated in FIG. 2 are recorded in the memory circuitry 35 in the form of programs executable by a computer. The processing circuitry 37 is a processor that reads out respective programs from the memory circuitry 35 and executes the programs to realize the function corresponding to each program. In other words, the processing circuitry 37 in a state having read out the respective programs has the respective functions illustrated in the processing circuitry 37 in FIG. 2. The processing circuitry 37 described in the first embodiment is an example of a processing circuitry described in the scope of claims.

The control function 37a executes entire control of the X-ray CT apparatus 100. For example, the control function 37a executes control related to scan, control related to reconstruction of CT image data and generation of various images from the CT image data, and display control of the generated various images described above.

The analysis function 37b performs fluid analysis based on the CT image data. Specifically, the analysis function 37b extracts time-series blood-vessel shape data representing the shape of blood vessels from three-dimensional CT image data. For example, the analysis function 37b reads out the CT image data in the plurality of time phases collected over time from the memory circuitry 35, and performs image processing with respect to the read CT image data in the read time phases, thereby extracting the time-series blood-vessel shape data.

The analysis function 37b sets a target region of which index value is calculated in a blood vessel region included in the CT image data. Specifically, the analysis function 37b sets a target region in the blood vessel region by an instruction of an operator via the input circuitry 31 or by image processing. The analysis function 37b extracts from the CT image data, as the blood-vessel shape data in the set target region, for example, a blood vessel core line (coordinate information of the core line), a cross-sectional area of the blood vessel and a lumen in a cross section vertical to the core line, and a distance from the core line to an inner wall and a distance from the core line to an outer wall in a columnar direction on a cross section vertical to the core line. The analysis function 37b can extract various pieces of blood-vessel shape data according to the analysis method.

The analysis function 37b sets analysis conditions for fluid analysis. Specifically, the analysis function 37b sets a physical value of blood, conditions for iterative calculation, and initial values for the analysis as the analysis conditions. For example, the analysis function 37b sets the viscosity, the density, or the like of blood as the physical value of blood. Further, the analysis function 37b sets a maximum number of iterations, a relaxation coefficient, an acceptable value of a residual error, and the like in the iterative calculation as the conditions for the iterative calculation. The analysis function 37b sets, as the initial values for the analysis, a flow volume, a pressure, a fluid resistance, and a pressure boundary. The various values used by the analysis function 37b can be set in the system in advance or can be defined interactively by an operator.

The analysis function 37b sets a portion to be treated in the blood vessel in the image data. Specifically, the analysis function 37b sets the portion to be treated in the blood vessel manually or automatically. For example, the analysis function 37b sets a range accepted via the input circuitry 31 as the portion to be treated. In this case, the input circuitry 31 accepts a range of which analysis conditions are changed (a portion to be treated) and the analysis function 37b sets the accepted range as the portion to be treated. Further, the analysis function 37b automatically sets the portion to be treated based on the shape in the target region. For example, the analysis function 37b extracts a stenosis portion based on the shape in the target region, and sets a stenosis portion having a certain degree of stenosis or higher, of the extracted stenosis portion, as the portion to be treated. Extraction of the stenosis portion can be performed by using an arbitrary method.

The analysis function 37b calculates the index value regarding the blood flow of the blood vessel by the fluid analysis using the image data including the blood vessels. Specifically, the analysis function 37b performs the fluid analysis using the blood-vessel shape data and the analysis conditions, to calculate an index value (fluid parameter) regarding the blood flow in the target region of the blood vessel. For example, the analysis function 37b calculates the index value such as the pressure, the flow volume of blood, the flow rate of blood, the vector, and the shear stress for each of predetermined positions in the blood vessel, based on the blood-vessel shape data such as the profile of the lumen and the outer wall of the blood vessel, a cross-sectional area of the blood vessel, and the core line, and setting conditions such as the physical value of blood, the conditions for the iterative calculation, and the initial values for the analysis. The analysis function 37b further calculates the index value such as the FFR from the calculated index value.

Figure 3:
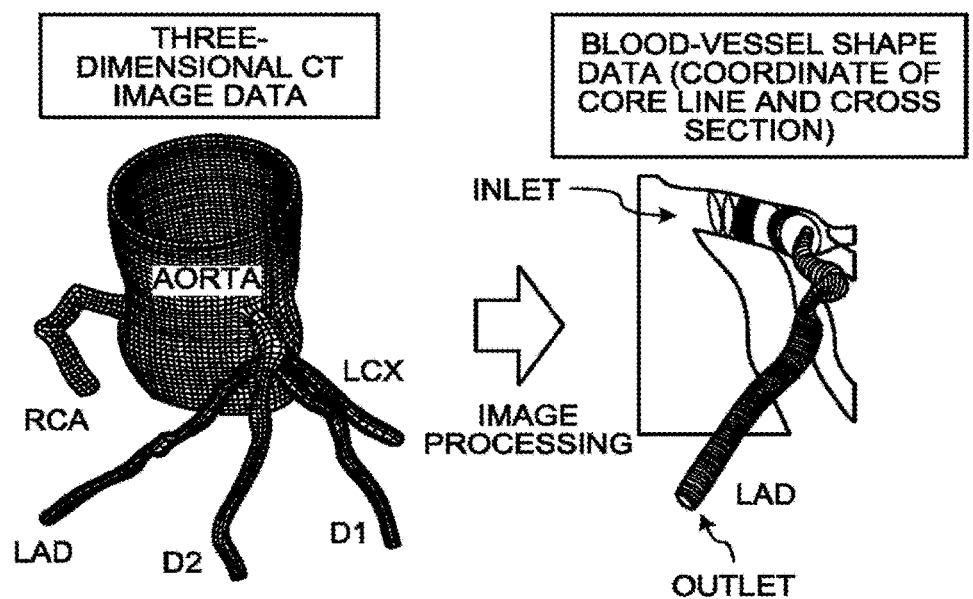
FIG. 3 is an explanatory diagram of an example of processing performed by an analysis function according to the first embodiment.

FIG. 3 is an explanatory diagram of an example of processing performed by the analysis function 37b according to the first embodiment. As illustrated in FIG. 3, for example, the analysis function 37b extracts blood-vessel shape data including the coordinate of a core line and cross section information for an LAD being a target region, from three-dimensional CT image data including a main artery and a coronary artery. Further, the analysis function 37b sets the analysis conditions for the analysis targeting in the extracted LAD. Further, the analysis function 37b performs the fluid analysis using the extracted blood-vessel shape data of the LAD and the set conditions, to calculate index values of the pressure, the flow volume of blood, the flow rate of blood, the vector, and the shear stress for each of predetermined positions along the core line, for example, from an inlet boundary to an outlet boundary of the target region LAD. That is, the analysis function 37b calculates the distribution of the pressure, the flow volume of blood, the flow rate of blood, the vector, and the shear stress for the target region. The analysis function 37b calculates the FFR at respective positions in the target region, for example, based on the calculated pressure distribution.

As described above, the analysis function 37b extracts the blood-vessel shape data respectively from CT image data in a plurality of time phases collected over time, and performs fluid analysis using the extracted blood-vessel shape data in the time phases and the analysis conditions, to calculate the index value regarding the blood flow. To obtain a highly accurate analysis result at the time of performing the fluid analysis of the coronary artery, it is desired that the plurality of time phases include a change of the shape of the coronary artery (for example, a change of the cross-sectional area) as much as possible, and the CT image data in each time phase is as sharp as possible. That is, it is desired to use CT image data in a time phase in which movement (blurring) of image due to pulsation is small, while the time-series blood-vessel shape data includes a series of changes from a time phase in which the area of the coronary artery becomes maximum due to inflow of blood to a time phase in which the area thereof becomes minimum due to outflow of blood as much as possible. Therefore, according to the first embodiment, the selection function 37c selects a time phase corresponding to the CT image data described above, from the respective time phases of the CT image data collected over time.

The selection function 37c selects a time phase in which blurring of image due to pulsation is small, while including a change of the shape of the coronary artery, from the CT image data in the plurality of time phases collected over time. Specifically, the selection function 37c selects a plurality of time phases from respective time phases corresponding to the plurality of pieces of CT image data, so that the time phases have relatively small movement with pulsation and a time interval between the time phases becomes large. More specifically, the selection function 37c extracts a range of time phases in which the movement with pulsation is relatively small in the respective time phases corresponding to the plurality of pieces of CT image data. Further, the selection function 37c selects a plurality of time phases so that the time phases have relatively small movement with pulsation and the time interval between the time phases becomes large, from the time phases included in the extracted range based on evaluation of the movement with pulsation in the pieces of image data corresponding to the time phases included in the extracted range.

The selection function 37c evaluates the movement with heartbeats of the heart and selects a plurality of time phases so that the time phases have relatively small movement with pulsation and the time intervals between the time phases become large. That is, the selection function 37c respectively acquires an image index for each of the pieces of CT image data. The selection function 37c extracts a set of CT image data from combinations of the CT image data having a larger time interval than a predetermined time interval of the pieces of CT image data, based on the image index in the respective pieces of image data. For example, the selection function 37c extracts a set of CT image data having an image quality index in the respective pieces of CT image data being equal to or larger than a predetermined threshold from the combinations of CT image data. The image quality index is an example of the image index. An example of selection of the plurality of time phases (selection of a set of CT image data) based on the image quality index is described below.

Figure 4:
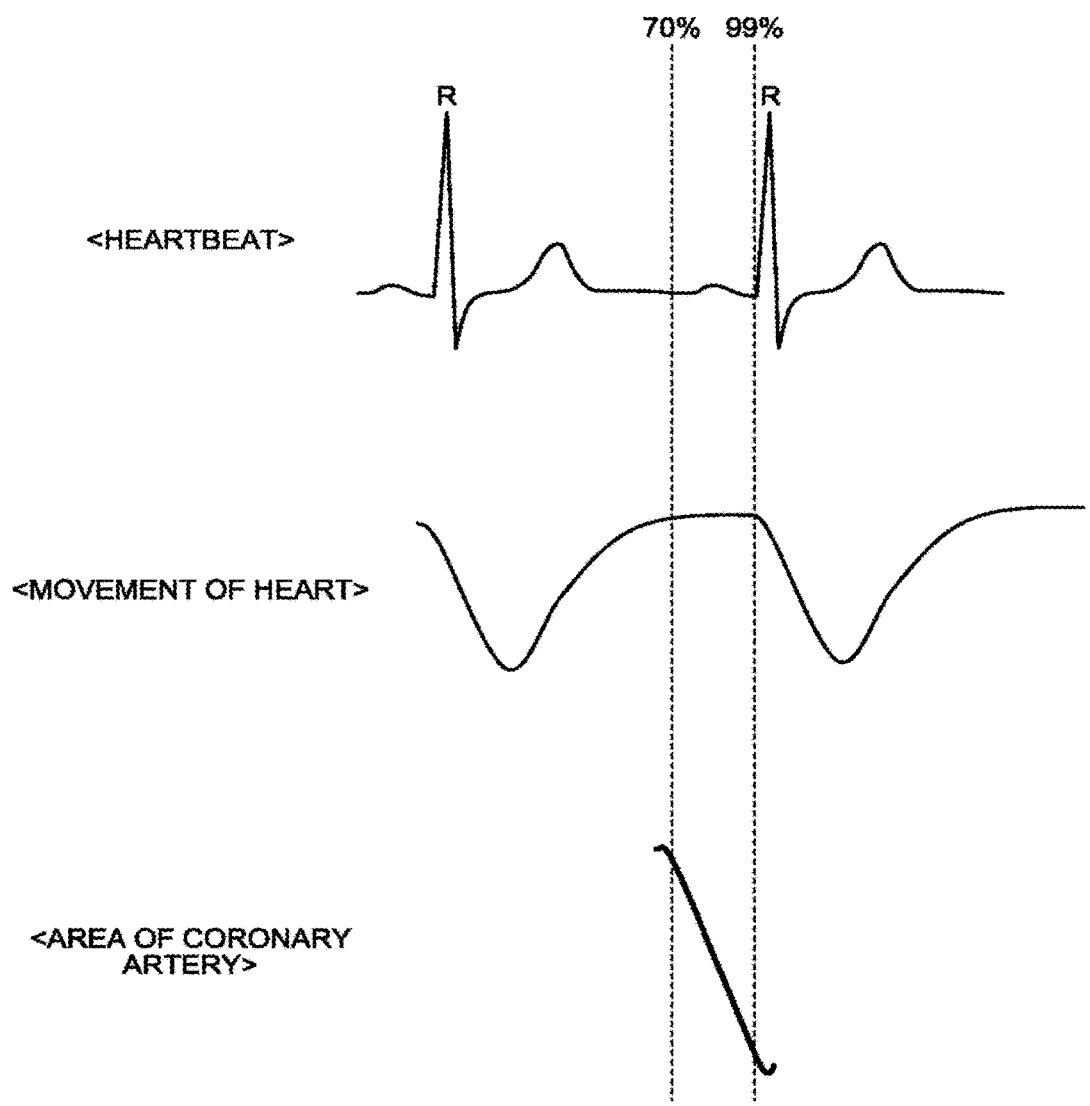
FIG. 4 is an explanatory diagram of selection of a time phase by a selection function according to the first embodiment.

FIG. 4 is an explanatory diagram of selection of a time phase by the selection function 37c according to the first embodiment. In FIG. 4, heartbeats are illustrated in an upper stage, movement of the heart is illustrated in a middle stage, and an area of a coronary artery is illustrated in a lower stage. In FIG. 4, the lateral direction illustrates time and time changes in the heartbeats, the movement of the heart, and the area of the coronary artery are illustrated in association with each other. For example, the selection function 37c selects a cardiac phase included in a range of cardiac phases 70% to 99%. The range of cardiac phases 70% to 99% includes time phases in which, as illustrated in FIG. 4, the movement of the heart is little and a change in the area of the coronary artery is large. The heart moves by contraction and expansion, and as illustrated in the middle stage of FIG. 4, the movement thereof is stabilized during a latter half of diastole (cardiac phases 70% to 99%). The selection function 37c selects the cardiac phase included in the cardiac phases 70% to 99% in which the movement of the heart is stabilized, thereby selecting a time phase in which the movement with pulsation is relatively small. The cardiac phases 70% to 99% correspond to a Wave Free Period. The Wave Free Period is time phases in the middle of diastole in which there is no influence of ejection pressure from pulse propagating downward in the coronary artery and reflection pressure formed by a left ventricular pressure and propagating in the coronary artery in a retrograde manner.

As illustrated in the lower stage of FIG. 4, the area of the coronary artery becomes maximum near the cardiac phase 70% and becomes minimum near the cardiac phase 99%. This is because blood starts to flow into the coronary artery near the cardiac phase 70% and flows out as progressing toward the cardiac phase 99%. The selection function 37c selects a plurality of time phases so as to include the area change of the coronary artery as much as possible so that the time intervals between the time phases become large as much as possible in the range of the cardiac phases 70% to 99%.

Figure 5:
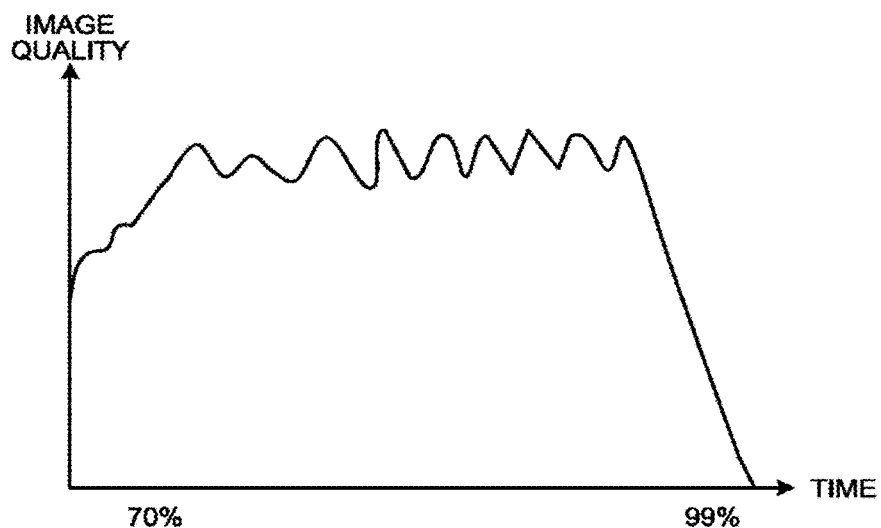
FIG. 5 is a diagram illustrating an example of a change in image quality of respective cardiac phases according to the first embodiment.

In the cardiac phases 70% to 99%, the movement of the heart is little and stable. But in CT image data actually collected, the image quality fluctuates. Further, near the cardiac phase 99%, there is an influence of the next contraction of the heart, and blurring may occur. FIG. 5 is a diagram illustrating an example of a change in image quality of respective cardiac phases according to the first embodiment. In FIG. 5, a time is plotted on the horizontal axis and image quality is plotted on the vertical axis. For example, as illustrated in FIG. 5, the image quality of CT image data is gradually improved toward the vicinity of the cardiac phase 70% and shifts while fluctuating in the vicinity of certain image quality. The image quality of the CT image data significantly decreases near the cardiac phase 99%. In this manner, the image quality of the CT image data is not constant even in the range of the cardiac phases 70% to 99% and largely changes.

Therefore, the selection function 37c respectively evaluates the movement with pulsation of the CT image data corresponding to the cardiac phases 70% to 99% in which the movement with pulsation is relatively small, to select a cardiac phase having smaller movement with pulsation from the cardiac phases 70% to 99%. The selection function 37c selects a cardiac phase having smaller movement with pulsation from the cardiac phases 70% to 99% so that the time interval increases further. The processing performed by the selection function 37c is described below, for a case where the selection function 37c selects four cardiac phases from the cardiac phases 70% to 99% as an example.

In this case, the selection function 37c selects a plurality of cardiac phases so that the respective time intervals between the adjacent cardiac phases in the plurality of time phases are large and approximate to each other. For example, when selecting four cardiac phases from the cardiac phases 70% to 99%, the selection function 37c selects four cardiac phases so that the CT image data of each cardiac phase has smaller movement with pulsation and the time intervals be the adjacent cardiac phases are approximated to an equal interval. This is because the fluid analysis of the coronary artery also analyses how the area of the coronary artery fluctuates (tendency of fluctuation) described above, and thus it is desired that the cardiac phases in the CT image data applied to the fluid analysis have an equal interval therebetween as much as possible.

Figure 6:
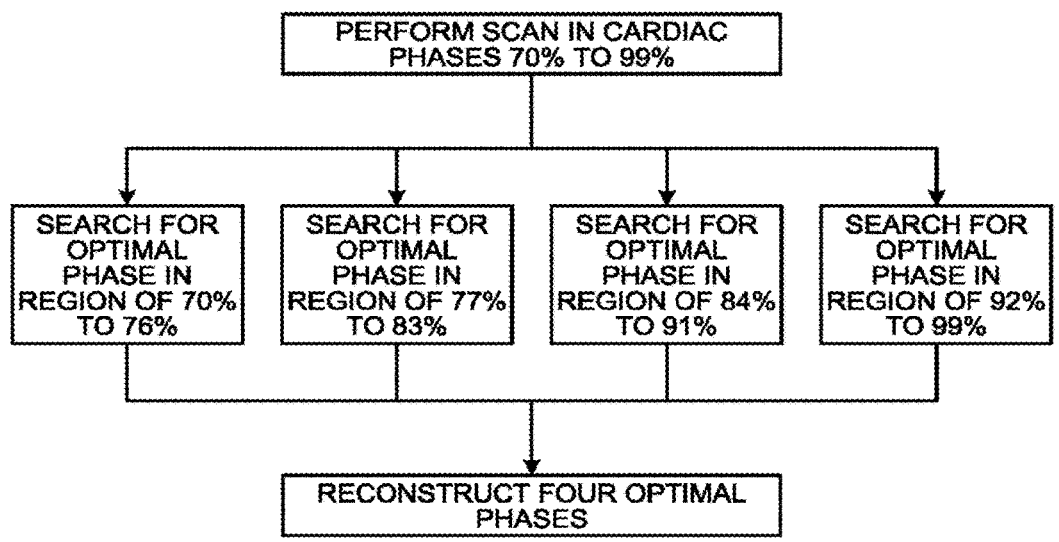
FIG. 6 is an explanatory diagram of an example of selection processing performed by the selection function according to the first embodiment.

An example of the selection processing of four cardiac phases performed by the selection function 37c is described below. For example, the selection function 37c divides the range (a Wave Free Period) into a plurality of partial ranges, and respectively selects a time phase having relatively small movement with pulsation among the time phases included in the partial range, for each partial range. That is, the selection function 37c divides the cardiac phases 70% to 99% into four regions, and selects one cardiac phase each from the divided respective regions. FIG. 6 is an explanatory diagram of an example of the selection processing performed by the selection function 37c according to the first embodiment. For example, the selection function 37c divides the cardiac phases 70% to 99% into four regions of "70% to 76%", "77% to 83%", "84% to 91%", and "92% to 99%", and searches for and selects an optimal phase in each region. The pieces of CT image data in four optimal cardiac phases are reconstructed from the respective pieces of cardiac phase data corresponding to the four cardiac phases selected from the respective regions by the selection function 37c.

Search of an optimal cardiac phase in the respective regions illustrated in FIG. 6 is, for example, to search for a cardiac phase having smaller movement with pulsation. For example, the selection function 37c evaluates the degree of blurring (definition) in an image by using the cardiac phase data for every 1% in the projection data in the cardiac. phases 70% to 90% collected by an ECG-gated method, and selects cardiac phase data having the smallest blurring in the image as the cardiac phase data to be reconstructed.

Figure 7:
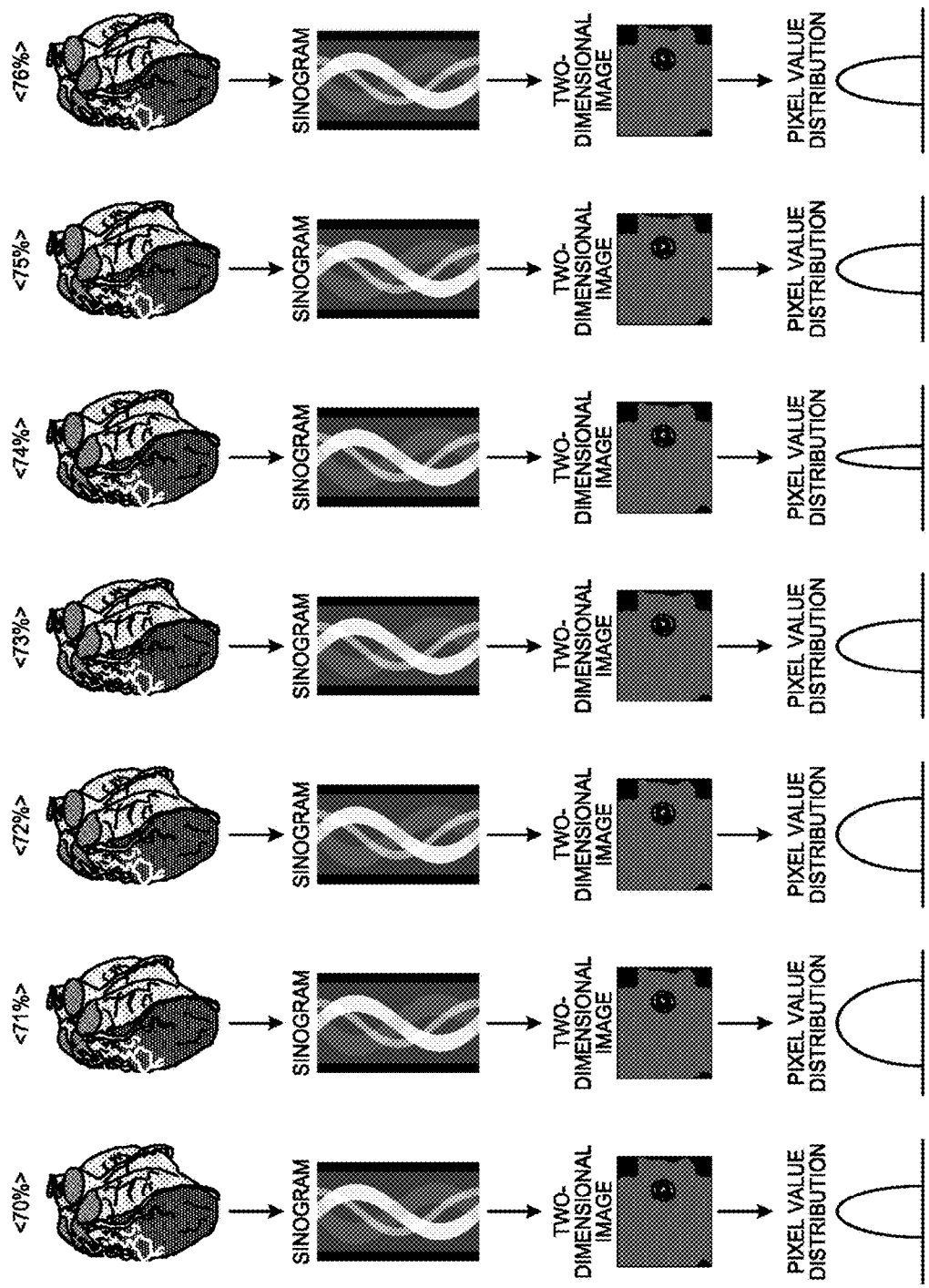
FIG. 7 is an explanatory diagram of an example of search processing of an optimal cardiac phase by the selection function according to the first embodiment.

FIG. 7 is an explanatory diagram of an example of search processing of an optimal cardiac phase by the selection function 37c according to the first embodiment. FIG. 7 illustrates a case where an optimal cardiac phase in a region of "70% to 76%" is searched. For example, the selection function 37c respectively extracts a sinogram of one slice including the coronary artery from the pieces of projection data for a plurality of heartbeats. As illustrated in FIG. 7, the selection function 37c respectively extracts cardiac phase data of "70%", cardiac phase data of "71%", cardiac phase data of "72%", cardiac phase data of "73%", cardiac phase data of "74%", cardiac phase data of "75%", and cardiac phase data of "76%" from the extracted respective sinograms to perform reconstruction, thereby generating an image for one slice including the coronary artery in each cardiac phase.

The selection function 37c respectively calculates an SD value for the images in the respective generated cardiac phases, extracts an image having little blurring (having high definition) based on the calculated SD value, and selects the cardiac phase in the extracted image as the optimal cardiac phase. For example, the selection function 37c selects, as illustrated in FIG. 7, the cardiac phase "74%" in an image having a narrow bottom width in the distribution of signal intensity (pixel value) for each pixel in each image, as the optimal cardiac phase in the region of "70% to 76%". The SD value described above is a standard deviation of the signal intensity for each pixel included in an image, and an index value indicating characteristics of noise.

The selection function 37c performs the selection processing described above with respect to the three regions of "77% to 83%", "84% to 91%", and "92% to 99%", to select the optimal cardiac phase from the respective regions. When the optimal cardiac phase is selected from the respective regions as described above, the time interval in the optimal cardiac phase selected in each region may become large. For example, if an optimal cardiac phase in the region of "70% to 76%" is selected as "74%", and an optimal cardiac phase in the region of "77% to 83%" is selected as "77%", the time interval becomes for "3%". As described above, in CT image data to be used for fluid analysis, it is desired that the time intervals between the cardiac phases are large and equal.

Figure 8:
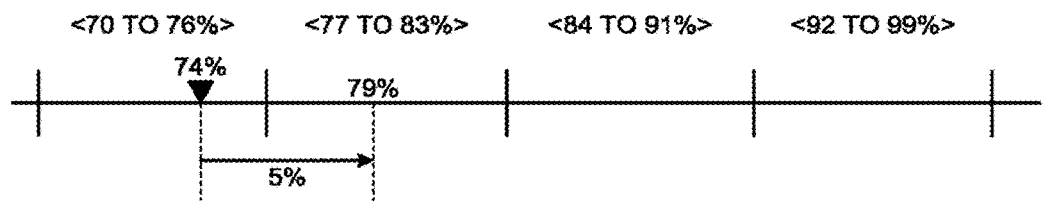
FIG. 8 is an explanatory diagram of an example of threshold processing performed by the selection function according to the first embodiment.

Therefore, the selection function 37c selects a plurality of cardiac phases in the cardiac phases included in the range, so that the time intervals between the cardiac phases become equal to or larger than a predetermined threshold. FIG. 8 is an explanatory diagram of an example of threshold processing performed by the selection function 37c according to the first embodiment. For example, the selection function 37c performs selection processing by using "5%" as the threshold of the time interval, as illustrated in FIG. 8. As an example, when selecting "74%" as the optimal cardiac phase in the region of "70% to 76%", the selection function 37c searches for an optimal cardiac phase in the region of "77% to 83%", designating "79%" having an interval of "5%" or more from "74%" as a lower bottom. That is, the selection function 37c searches for the optimal cardiac phase in the region of "79% to 83%". The threshold of the time interval can be arbitrarily set.

As described above, when the selection function 37c selects the optimal cardiac phase from the four regions of "70% to 76%", "77% to 83%", "84% to 91%", and "92% to 99%", the acquisition function 37d acquires the pieces of cardiac phase data corresponding to the plurality of time phases selected by the selection function 37c. Specifically, the acquisition function 37d acquires the cardiac phase data for reconstructing the CT image data of each of the selected optimal cardiac phases. That is, the acquisition function 37d acquires the cardiac phase data in each column in a body-axis direction for each of the selected optimal cardiac phases. The image reconstruction circuitry 36 reconstructs the three-dimensional CT image data in the four optimal cardiac phases by using the pieces of cardiac phase data corresponding to the acquired four optimal cardiac phases. The acquisition function 37d performs the fluid analysis described above by using the pieces of CT image data in the four reconstructed cardiac phases.

In the X-ray CT apparatus 100 according to the first embodiment, if the optimal cardiac phase selected by the selection function 37c does not comply with a predetermined condition, a warning can be presented. Specifically, the presentation function 37e presents a warning to an operator, if the cardiac phases selected by the selection function 37c do not comply with the predetermined condition. For example, if the time interval between the cardiac phases at an upper end and a lower end is smaller than a predetermined threshold in the selected optimal cardiac phase, the presentation function 37e causes the display 32 to display a warning. In this case, the presentation function 37e can display the warning and present an alternative proposal.

For example, the presentation function 37e presents a cardiac phase having the smallest movement with pulsation as an alternative proposal in a cardiac phase in which a time interval between cardiac phases at the upper end and the lower end becomes larger than the predetermined threshold.

Figure 9:
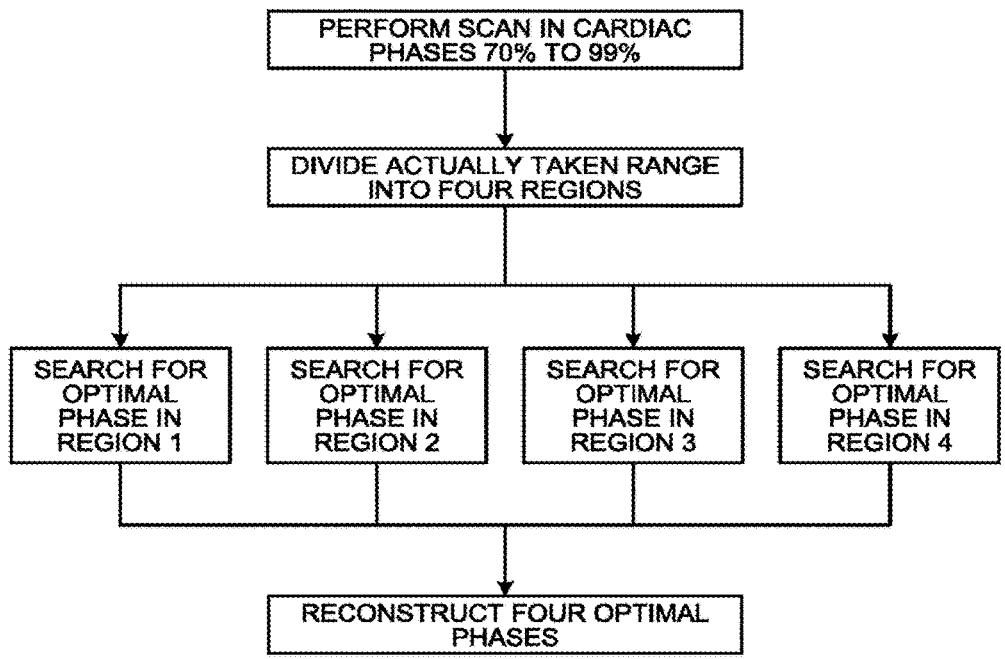
FIG. 9 is an explanatory diagram of an example of the selection processing performed by the selection function according to the first embodiment.

In the embodiment described above, a case in which the range of the cardiac phases "70% to 99%" is divided into four regions to perform processing has been described. However, there may be a case in which cardiac phase data in the range of the cardiac phases "70% to 99%" is not collected in the actual scan. Therefore, the selection function 37c can divide the actually collected cardiac phase range. FIG. 9 is an explanatory diagram of an example of the selection processing performed by the selection function according to the first embodiment. For example, the selection function 37c divides an actually collected cardiac phase range into four, of the pieces of projection data collected in the cardiac phases 70% to 99% in ECG-gated scan, and searches for and selects an optimal phase in each region. The pieces of CT image data in the four optimal cardiac phases are reconstructed from the respective pieces of cardiac phase data corresponding to the four cardiac phases selected from the respective regions by the selection function 37c.

As an example, when an actually collected cardiac phase range is "68% to 95%", the selection function 37c divides "68% to 95%" into four regions. The selection function divides the region so that the cardiac phases included in each region does not exceed the range of "70% to 99%". For example, the selection function 37c divides "68% to 95%" into four regions of "70% to 76%", "77% to 82%", "83% to 88%", and "89% to 95%", by excluding "68%" and "69%".

In the first embodiment described above, a case where an image for one slice is generated from the cardiac phase data to search for an optimal cardiac phase has been described as an example. However, the first embodiment is not limited thereto and, for example, the search for an optimal cardiac phase can be performed by reconstructing the pieces of CT image data corresponding to respective cardiac phases. In this case, for example, the selection function 37c can generate an image of a slice including a coronary artery from the reconstructed CT image data and search for an optimal cardiac phase by comparing SD values of the generated slices. Further, for example, the selection function 37c can extract a three-dimensional region of the coronary artery from the reconstructed CT image data and search for an optimal cardiac phase by comparing the SD values regarding the three-dimensional region (respective voxels) of the extracted coronary artery.

Further, in the first embodiment described above, a case where an optimal cardiac phase is selected respectively from each region has been described as an example. However, the first embodiment is not limited thereto and, for example, the upper end and the lower end of the range can be fixedly selected. As an example, the selection function 37c can select the cardiac phases "70%" and "99%" fixedly as the optimal cardiac phases in the range of the cardiac phases "70% to 99%". Alternatively, the selection function 37c can select at least the cardiac phase near the upper end and the cardiac phase near the lower end in the range as the plurality of cardiac phases. As an example, the selection function 37c can select preferentially near the cardiac phase "70%" and near the cardiac phase "99%" as the optimal cardiac phases in the range of the cardiac phases "70% to 99%".

Figure 10:
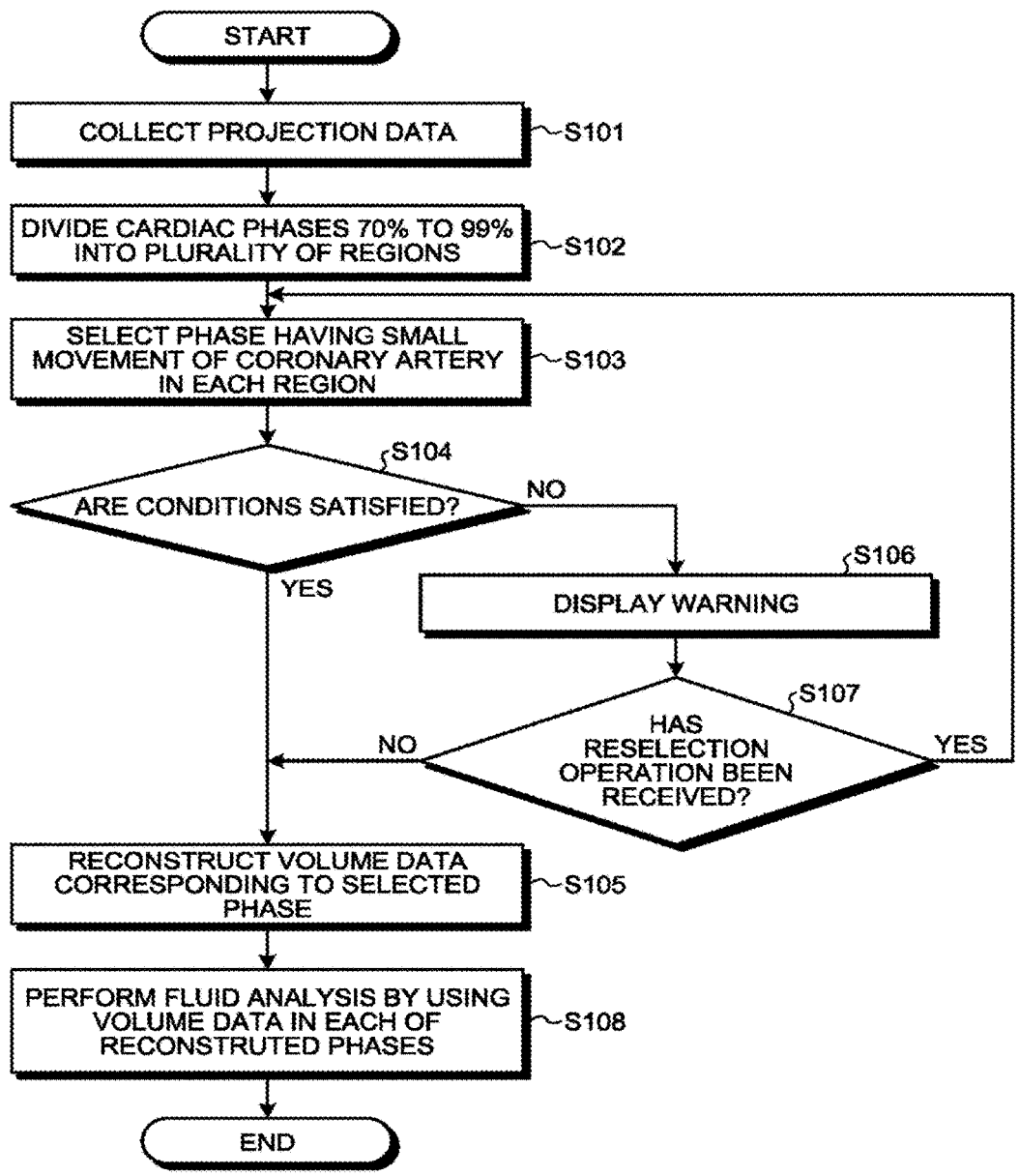
FIG. 10 is a flowchart illustrating a process procedure performed by the X-ray CT apparatus according to the first embodiment.

A process procedure by the X-ray CT apparatus 100 according to the first embodiment is described next. FIG. 10 is a flowchart illustrating a process procedure performed by the X-ray CT apparatus 100 according to the first embodiment. FIG. 10 illustrates a process procedure in a case where the range of the cardiac phases 70% to 99% is divided.

Step S101 in FIG. 10 is realized, for example, by invoking a program corresponding to the control function a from the memory circuitry 35 and executing the program by the processing circuitry 37. Steps S102, S103, and S107 are realized by invoking a program corresponding to the selection function 37c from the memory circuitry 35 and executing the program by the processing circuitry 37. Steps S104 and S106 are realized by invoking a program corresponding to the presentation function 37e from the memory circuitry 35 and executing the program by the processing circuitry 37. Step S105 is realized by reading out a corresponding program from the memory circuitry 35 and executing the program by the image reconstruction circuitry 36. Step S108 is realized by invoking a program corresponding to the analysis function 37b from the memory circuitry 35 and executing the program by the processing circuitry 37.

In the X-ray CT apparatus 100 according to the first embodiment, the processing circuitry 37 first collects pieces of projection data (Step S101). The processing circuitry 37 divides the cardiac phases 70% to 99% into a plurality of regions (Step S102), and selects a cardiac phase in which movement of a coronary artery is small in each region (Step S103). Subsequently, the processing circuitry 37 determines whether the selected cardiac phase satisfies the condition (Step S104). If the selected cardiac phase satisfies a certain condition (YES at Step S104), the image reconstruction circuitry 36 reconstructs volume data corresponding to the selected cardiac phase (Step 105).

On the other hand, if the selected cardiac phase does not satisfy the condition (NO at Step S104), the processing circuitry 37 displays a warning (Step S106). The processing circuitry 37 then determines whether a reselection operation has been received (Step S107). If a reselection operation has been received (YES at Step S107), the processing circuitry 37 returns to Step S103, to select a cardiac phase having small movement of the coronary artery. On the other hand, if a reselection operation has not been received (NO at Step S107), the image reconstruction circuitry 36 reconstructs the volume data corresponding to the selected cardiac phase (Step S105). At Step S105, when the volume data corresponding to each cardiac phase is reconstructed, the processing circuitry 37 performs fluid analysis by using the reconstructed volume data of each cardiac phase (Step S108).

As described above, according to the first embodiment, the data collection circuitry 14 collects a plurality of pieces of projection data over time. The selection function 37c selects a plurality of cardiac phases from the respective time phases corresponding to the pieces of projection data, so that the cardiac phase has relatively small movement with pulsation and the time intervals between the time phases become large. The acquisition function 37d acquires the pieces of projection data corresponding to the cardiac phases selected by the selection function 37c. Therefore, the X-ray CT apparatus 100 according to the first embodiment enables to acquire appropriate data easily at the time of performing fluid analysis.

According to the first embodiment, the selection function 37c extracts a range of the cardiac phases having relatively small movement with pulsation in respective time phases corresponding to the pieces of projection data. The selection function 37c selects a plurality of cardiac phases in which the cardiac phases have relatively small movement with pulsation and the time intervals between the cardiac phases become large from the cardiac phases included in the range, based on evaluation of movement with pulsation in the pieces of image data corresponding to the cardiac phases included in the extracted range. Therefore, the X-ray CT apparatus 100 according to the first embodiment enables to acquire more appropriate data at the time of performing the fluid analysis.

Further, according to the first embodiment, the selection function 37c evaluates the movement with pulsation based on the definition in a coronary artery region included in the projection data. Therefore, the X-ray CT apparatus 100 according to the first embodiment enables to evaluate the movement with pulsation easily.

According to the first embodiment, the selection function 37c divides the range into a plurality of partial ranges, and selects a cardiac phase having relatively small movement with pulsation from the cardiac phases included in the respective partial range. Further, the selection function 37c divides the range into partial ranges so that the widths of the partial ranges are approximate to each other. Therefore, the X-ray CT apparatus 100 according to the first embodiment enables to select cardiac phases having a certain interval easily.

According to the first embodiment, the selection function 37c selects at least a cardiac phase near an upper end and a cardiac phase near a lower end in the range as the plurality of cardiac phases. Therefore, the X-ray CT apparatus 100 according to the first embodiment enables to select cardiac phases close to a cardiac phase in which the area of the coronary artery becomes maximum and a cardiac phase in which the area of the coronary artery becomes minimum easily.

According to the first embodiment, the selection function 37c selects the plurality of cardiac phases so that the time intervals between the cardiac phases become equal to or larger than a predetermined threshold, in the cardiac phases included in the range. Therefore, the X-ray CT apparatus 100 according to the first embodiment enables that the time intervals between the cardiac phases are approximated to an equal interval.

According to the first embodiment, the selection function 37c selects a plurality of cardiac phases so that the respective time intervals between adjacent cardiac phases are large and approximate to each other in the plurality of cardiac phases. Therefore, the X-ray CT apparatus 100 according to the first embodiment enables that the time intervals between cardiac phases are increased and approximated to an equal interval.

Further, according to the first embodiment, the presentation function 37e presents a warning to an operator if the cardiac phases selected by the selection function 37c do not comply with a predetermined condition. Therefore, the X-ray CT apparatus 100 according to the first embodiment enables to suppress execution of fluid analysis using inappropriate CT image data in advance.

Second Embodiment

A second embodiment is described next. A configuration of the X-ray CT apparatus 100 according to the second embodiment is basically the same as that of the X-ray CT apparatus 100 illustrated in FIG. 2. Therefore, in the following descriptions, features different from those of the X-ray CT apparatus 100 according to the first embodiment are mainly explained, and constituent elements having functions identical to those of the constituent elements illustrated in FIG. 2 are denoted by like reference signs and detailed descriptions thereof will be omitted.

In the first embodiment described above, a case where the range of cardiac phases is divided into a plurality of regions to select an optimal cardiac phase has been described as an example. In the second embodiment, a case where an optimal cardiac phase is selected without dividing the range of cardiac phases is described. For example, the X-ray CT apparatus 100 according to the second embodiment respectively evaluates the movement with pulsation with respect to all the cardiac phases to select an optimal cardiac phase based on an evaluation result.

Figure 11:
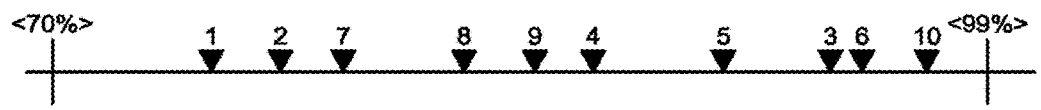
FIG. 11 is an explanatory diagram of an example of selection processing performed by a selection function according to a second embodiment.

FIG. 11 is an explanatory diagram of an example of selection processing performed by the selection function according to the second embodiment. FIG. 11 illustrates a case where an optimal cardiac phase is selected from the range of the cardiac phases 70% to 99%. For example, the selection function 37c respectively calculates the SD value described above regarding the cardiac phase for each 1% in the range of the cardiac phases 70% to 99%. As illustrated in FIG. 11, the selection function 37c ranks the respective cardiac phases in the order of having a lower SD value to select an optimal cardiac phase. The selection function 37c does not simply select a cardiac phase in the order from a cardiac phase having a higher rank, but also takes the time interval between the cardiac phases into consideration to select the optimal cardiac phase. As an example, the selection function 37c selects the optimal cardiac phase so that the time interval between the cardiac phases is equal to or larger than "5%" and the evaluation rank by the SD value becomes high.

Also in the second embodiment, there can be a case where near an upper end and near a lower end of the range (for example, 70% to 99%) are preferentially selected as the optimal cardiac phase. In this case, the selection function 37c first selects a cardiac phase having a higher rank near the upper end and the lower end of the range respectively as the optimal cardiac phases. The selection function 37c further selects an optimal cardiac phase from the cardiac phases away from the selected optimal cardiac phases by a predetermined time interval (for example, "5%") or more.

Figure 12:
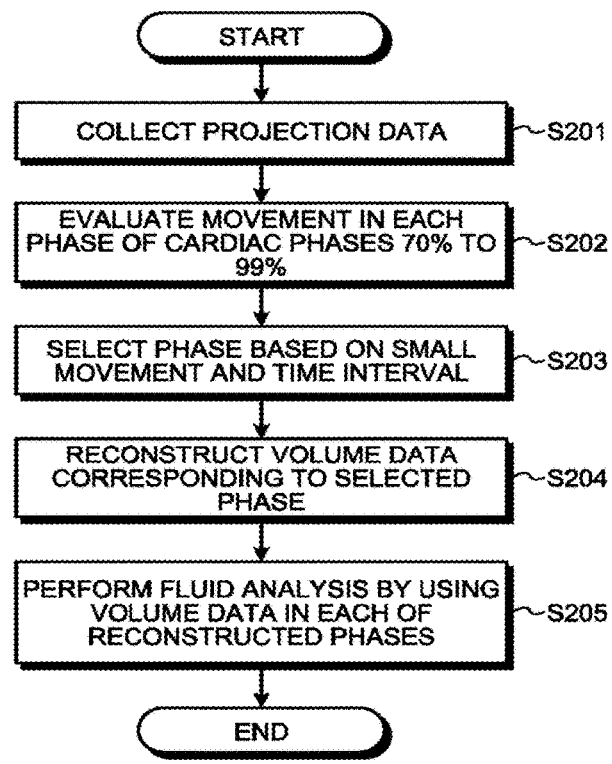
FIG. 12 is a flowchart illustrating a process procedure performed by an X-ray CT apparatus according to the second embodiment.

A process procedure performed by the X-ray CT apparatus 100 according to the second embodiment is described next. FIG. 12 is a flowchart illustrating a process procedure performed by the X-ray CT apparatus 100 according to the second embodiment. FIG. 12 illustrates the process procedure in a case where an optimal cardiac phase is selected from the range of the cardiac phases 70% to 99%.

Step S201 in FIG. 12 is realized, for example, by invoking a program corresponding to the control function 37a from the memory circuitry 35 and executing the program by the processing circuitry 37. Steps S202 and S203 are realized by invoking a program corresponding to the selection function 37c from the memory circuitry 35 and executing the program by the processing circuitry 37. Step S204 is realized by reading out a corresponding program from the memory circuitry 35 and executing the program by the image reconstruction circuitry 36. Step S205 is realized by invoking a program corresponding to the analysis function 37b from the memory circuitry 35 and executing the program by the processing circuitry 37.

In the X-ray CT apparatus 100 according to the second embodiment, the processing circuitry 37 first collects pieces of projection data (Step S201). The processing circuitry 37 then evaluates the movement in each cardiac phase of the cardiac phases 70% to 99% (Step S202). The processing circuitry 37 selects a cardiac phase based on small movement and the time interval (Step S203). Thereafter, the image reconstruction circuitry 36 reconstructs the volume data corresponding to the selected cardiac phase (Step S204). At Step S204, when the volume data corresponding to each cardiac phase is reconstructed, the processing circuitry 37 performs fluid analysis by using the reconstructed volume data in each cardiac phase (Step S205).

As described above, according to the second embodiment, the selection function 37c evaluates the movement with pulsation for each cardiac phase included in the range of the cardiac phase having relatively small movement with pulsation to select an optimal cardiac phase. Therefore, the X-ray CT apparatus 100 according to the second embodiment enables to acquire appropriate data at the time of performing fluid analysis.

Third Embodiment

While the first and second embodiments have been described above, the present invention can be also carried out in various different modes other than the first and second embodiments described above.

The selection processing of an optimal cardiac phase described in the first and second embodiments can be performed at an arbitrary timing. For example, the selection function 37c selects a plurality of optimal cardiac phases at the time of data transfer. As an example, the selection function 37c selects an optimal cardiac phase by using the volume data at the time of transferring the reconstructed volume data to the medical information processing apparatus 300 or the like. Alternatively, the selection function 37c selects the plurality of optimal cardiac phases at the time of activation of a fluid analysis application. As an example, the selection function 37c selects the optimal cardiac phase when an operation for activating the fluid analysis application has been received via the input circuitry 31. In this case, the selection function 37c can perform the selection processing by using the cardiac phase data, or by using the volume data (CT image data).

In the embodiments described above, as an image index, a case of using thane image quality index has been described as an example. However, the embodiment is not limited thereto, and the X-ray CT apparatus 100 can use various kinds of image indexes. For example, the X-ray CT apparatus 100 can use extraction performance of a portion as the image index. The X-ray CT apparatus 100 can perform extraction processing of a shape of a portion such as the blood-vessel shape data described above. The extraction accuracy of a portion from the CT image data varies depending on the condition of the collected pieces of CT image data. For example, if movement with pulsation of the heart is large, the accuracy of extracting a portion may decrease. That is, the X-ray CT apparatus 100 according to a third embodiment uses the extraction performance of a portion attributable to the image data as the image index.

Specifically, the selection function 37c according to the third embodiment extracts a set of CT image data to be used for fluid analysis from a combination of pieces of CT image data, based on an extraction result of a predetermined portion included in the respective pieces of CT image data. The selection function 37c uses as the predetermined portion, for example, a blood vessel wall of a coronary artery or a core line of the coronary artery. An example of selection of a plurality of time phases (selection of a set of CT image data) based on the extraction performance of these portions is described below.

The X-ray CT apparatus 100 according to the third embodiment reconstructs the CT image data in each time phase at the time of extraction of a portion. That is, the image reconstruction circuitry 36 reconstructs the CT image data corresponding to each cardiac phase from the collected pieces of projection data for a plurality of heartbeats. For example, the image reconstruction circuitry 36 respectively reconstructs the pieces of CT image data of the respective cardiac phases from the respective pieces of cardiac phase data of the cardiac phases 70% to 99%.

When the pieces of CT image data of the respective cardiac phases are reconstructed, the analysis function 37b extracts a portion from the CT image data of each cardiac phase. The analysis function 37b can extract a portion from the CT image data of each cardiac phase by various methods. For example, the analysis function 37b extracts the blood vessel wall and the core line by performing the extraction processing respectively with respect to the respective pieces of CT image data. That is, the analysis function 37b extracts respective portions from all the pieces of CT image data by performing portion extraction with respect to all the pieces of CT image data reconstructed by the image reconstruction circuitry 36. The analysis function 37b can use an existing algorithm appropriately as an extraction algorithm to be used for the portion extraction.

The analysis function 37b extracts a portion from the CT image data in one cardiac phase and performs alignment between the CT image data in the cardiac phase in which the portion has been extracted and the pieces of CT image data in other cardiac phases, thereby enabling to extract a portion in the CT image data in other cardiac phases. In this case, the analysis function 37b extracts the blood vessel wall and the core line by performing the extraction processing with respect to the CT image data in one cardiac phase first. The analysis function 37b then performs alignment between the CT image data in the cardiac phase in which the blood vessel wall and the core line have been extracted and the pieces of CT image data in other cardiac phases. For example, the analysis function 37b extracts a characteristic point respectively from the pieces of CT image data, for which alignment processing is to be performed, and performs alignment processing of a non-rigid body to be deformed to match the extracted characteristic points with each other.

As an example, the analysis function 37b respectively extracts a corresponding characteristic point (an anatomical characteristic point) from the CT image data in the cardiac phase in which the blood vessel wall and the core line have been extracted and the pieces of CT image data in other cardiac phases. The analysis function 37b then calculates coordinate transformation information for matching the extracted respective characteristic points with each other. For example, the analysis function 37b calculates coordinate transformation information in a three-dimensional coordinate system for matching the characteristic points in the pieces of CT image data in other cardiac phases with the characteristic point in the CT image data in the cardiac phase in which the blood vessel wall and the core line have been extracted. That is, the analysis function 37b calculates transformation information for calculating positions corresponding to the respective positions in the CT image data in the cardiac phase in which the blood vessel wall and the core line have been extracted, in the CT image data in other cardiac phases. The analysis function 37b can specify coordinates of the blood vessel wall and the core line in the CT image data in other cardiac phases by using the transformation information with respect to the extracted coordinates of the blood vessel wall and the core line.

Figure 13:
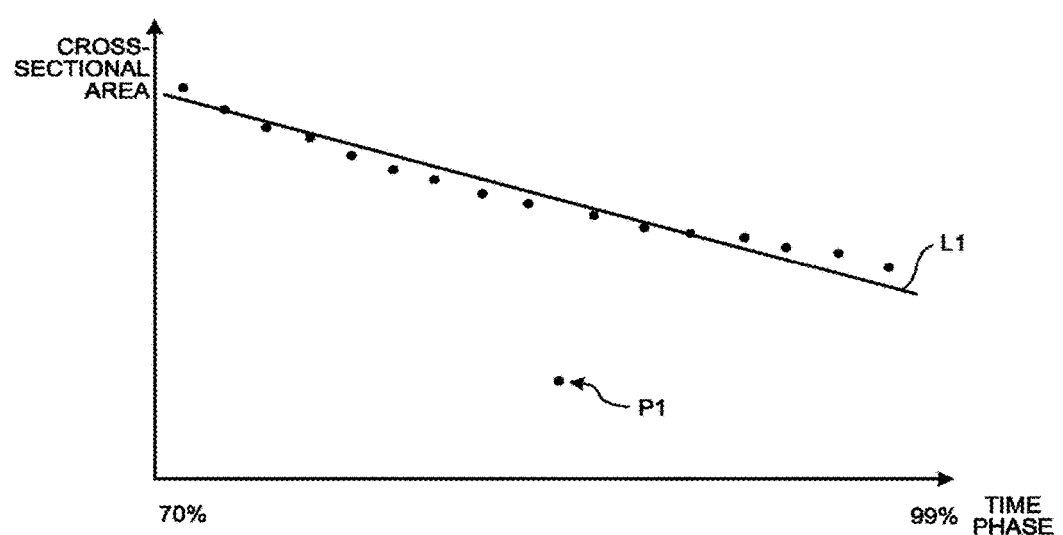
FIG. 13 is an explanatory diagram of selection of a time phase by a selection function according to a third embodiment.

As described above, when a portion has been extracted, the selection function 37c selects a plurality of time phases (a set of CT image data) based on an extraction result. A case of using an extraction result of a blood vessel wall of a coronary artery and a case of using an extraction result of a core line of the coronary artery is described in this order. For example, the selection function 37c selects a plurality of time phases based on fluctuations of a cross-sectional area of the blood vessel wall extracted by the analysis function 37b. FIG. 13 is an explanatory diagram of selection of a time phase by the selection function 37c according to the third embodiment. In FIG. 13, a time phase is plotted on a horizontal axis and a cross-sectional area is plotted on a vertical axis. For example, the selection function 37c calculates a cross-sectional area of a predetermined cross section in the blood vessel wall extracted by the analysis function 37b, as illustrated by dots in the graph of FIG. 13, respectively for respective pieces of CT image data. The selection function 37c compares an inclination of a straight line L1 indicating a general change of the cross-sectional area of the coronary artery with the calculated cross-sectional areas of the respective cardiac phases, and excludes CT image data of the cardiac phase inappropriate as a chronological change of the cross-sectional area from a selection target. For example, the selection function 37c excludes he CT image data in a cardiac phase P1 illustrated in FIG. 13 from the selection target. That is, the selection function 37c compares adjacent values of the cross-sectional area with each other, and excludes the CT image data in a cardiac phase having a large divergence degree from the value of the adjacent cross-sectional area from the selection target.

As an example, the selection function 37c first selects cardiac phases respectively from four regions of "70% to 76%", "77% to 83%", "84% to 91%", and "92% to 99%", so that the time interval between the cardiac phases becomes equal to or larger than a predetermined threshold. The selection function 37c calculates the cross-sectional area in the selected respective cardiac phases and compares he respective cross-sectional areas with each other. Further, the selection function 37c determines whether the cross-sectional area has changed exceeding an allowable range based on the inclination of the straight line L1. If the change of the cross-sectional area in the selected respective cardiac phases has not exceeded an allowable range based on the inclination of the straight line L1, the selection function 37c decides the cardiac phases selected from the four regions of "70% to 76%", "77% to 83%", "84% to 91%", and "92% to 99%" as the optimal cardiac phases.

On the other hand, if the change of the cross-sectional area in the selected respective cardiac phases has exceeded an allowable range based on the inclination of the straight line L1, the selection function 37c reselects a cardiac phase based on predetermined conditions. For example, if the change of the cross-sectional area in the cardiac phase selected from the region of "77% to 83%" has exceeded the allowable range, the selection function 37c selects a cardiac phase again from the region of "77% to 83%". The selection function 37c reselects a cardiac phase from the region of "77% to 83%" so as to maintain the time interval with the selected cardiac phases in the adjacent regions of "70% to 76%" and "84% to 91%" as much as possible.

For example, when reselecting a cardiac phase, the selection function 37c selects a cardiac phase adjacent to the cardiac phase determined as inappropriate. As an example, when having selected "79%" in the first selection, the selection function 37c selects a cardiac phase of "78%" or "80%".

Alternatively, when reselecting a cardiac phase, the selection function 37c selects a cardiac phase away by a predetermined number of phases (for example, 3%). As an example, when having selected "79%" in the first selection, the selection function 37c selects a cardiac phase of "82%". As described above, the extraction accuracy of a portion from the CT image data may decrease when the movement is large. Therefore, when a cardiac phase adjacent to the cardiac phase determined as inappropriate is reselected, the reselected cardiac phase may also become inappropriate. Therefore, the selection function 37c selects a cardiac phase away therefrom by a predetermined number of phases, thereby enabling to perform reselection accurately.

When reselecting the cardiac phase, the selection function 37c can readjust the time interval between the four cardiac phases. For example, when the cardiac phase of "79%" is determined as inappropriate and a cardiac phase of "82%" is reselected, the selection function 37c reselects the already selected cardiac phases from the regions of "84% to 91%" and "92% to 99%". That is, the selection function 37c reselects a cardiac phase in the region of "84% to 91%" and a cardiac phase in the region of "92% to 99%" so that the time interval between the cardiac phases becomes large.

In the example described above, a case where the cross-sectional areas of a coronary artery in the respective cardiac phases selected from the four regions are calculated and compared with each other has been described. However, the embodiment is not limited thereto, and the cross-sectional areas of the coronary artery in all the cardiac phases can be calculated and compared with each other. In this case, for example, the selection function 37c calculates the cross-sectional area of the coronary artery in all the cardiac phases and selects a cardiac phase in which a change of the cross-sectional area does not exceed an allowable range based on the inclination of the straight line L1 and the time interval between cardiac phases becomes larger.

Further, in the example described above, a case where extraction of a blood vessel wall of a coronary artery is determined by using the cross-sectional area of the coronary artery has been described. However, the embodiment is not limited thereto, and for example, it can be used whether the blood vessel wall of the coronary artery has been extracted. In this case, for example, the selection function 37c excludes the CT image data in which the blood vessel wall ha not been extracted from the selection target. Further, for example, the selection function 37c can determine the extraction accuracy of the blood vessel wall by using similarity of a profile of the blood vessel wall. In this case, for example, the selection function 37c compares the profile of the blood vessel wall in the cardiac phase to be determined with the profiles of the blood vessel wall in the cardiac phases adjacent thereto on both sides, and if the similarity thereof both fall below a predetermined threshold, the selection function 37c excludes the cardiac phase to be determined from the selection target.

A case of using an extraction result of the core line of the coronary artery is described next. In this case, for example, the selection function 37c compares the lengths of the core line of the coronary artery extracted by the analysis function 37b with each other, to determine the extraction accuracy of the core line. For example, when the core line is respectively extracted from all the pieces of CT image data, there may be a case in which extraction of the core line fails and the length thereof becomes short. The selection function 37c respectively calculates the lengths of respective core lines extracted from the pieces of CT image data in respective cardiac phases. The selection function 37c compares the calculated lengths of the core lines between the respective cardiac phases and excludes the cardiac phase having a shorter length of the core line than other core lines from the selection target.

In the example described above, the case where the selection function 37c automatically performs reselection based on the extracted blood vessel wall and the core line has been described. However, the embodiment is not limited thereto, and for example, the extraction result can be presented to an operator to receive an instruction to perform reselection. In this case, for example, the presentation function 37e causes the display 32 to display the result of extraction processing of a portion by the analysis function 37b. The operator judges whether to perform reselection by referring to the result of extraction processing displayed on the display 32. The operator inputs an instruction whether to perform reselection via the input circuitry 31. If the input circuitry 31 receives an instruction to perform reselection, the selection function 37c reselects a cardiac phase. On the other hand, if the input circuitry 31 receives an instruction not to perform reselection, the analysis function 37b performs fluid analysis using the CT image data of the cardiac phase already selected.

Figure 14:
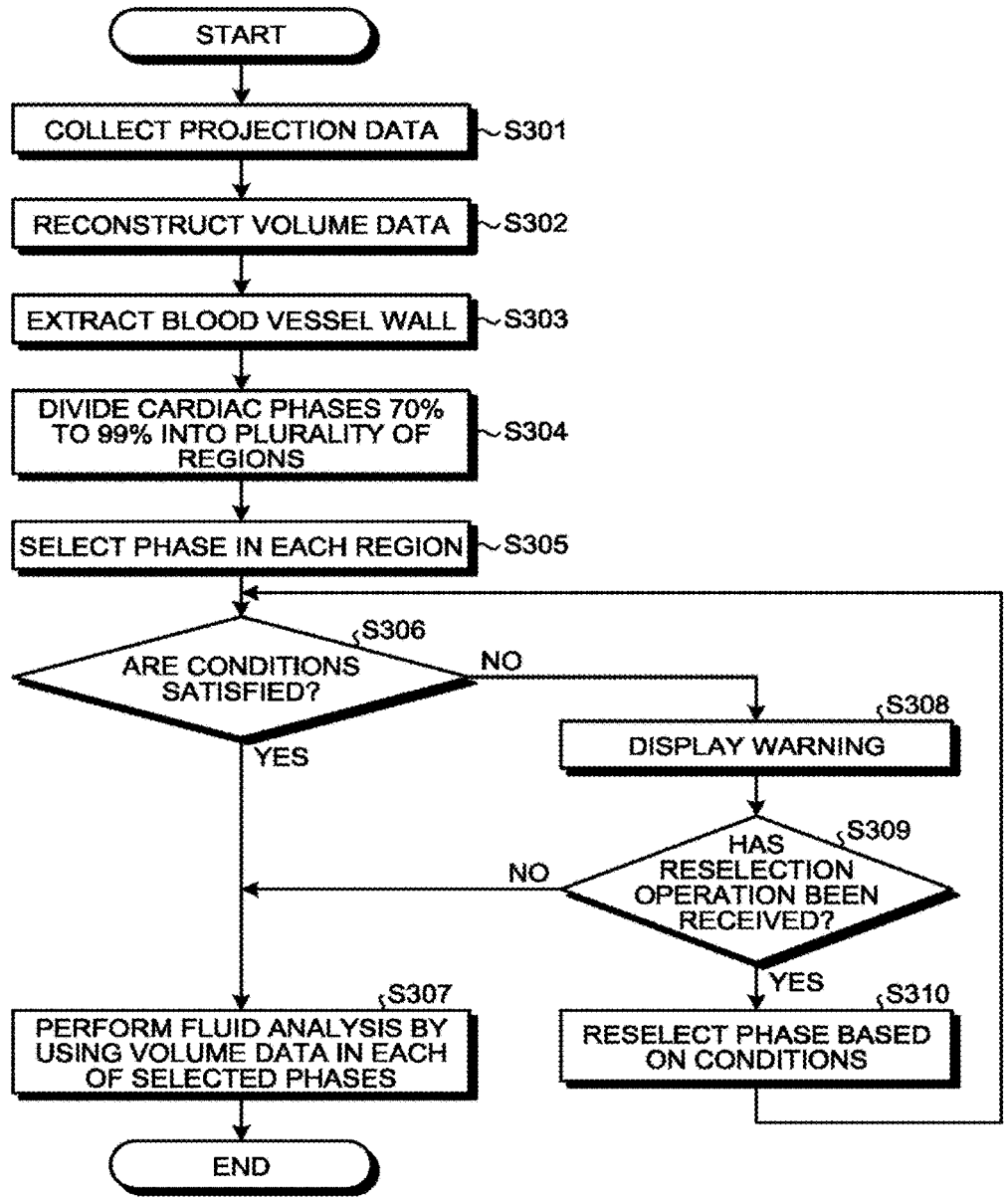
FIG. 14 is a flowchart illustrating a process procedure performed by an X-ray CT apparatus according to the third embodiment.

The example of using the extraction performance of a portion as an image index has been described. A process procedure performed by the X-ray CT apparatus 100 according to the third embodiment is described next. FIG. 14 is a flowchart illustrating the process procedure performed by the X-ray CT apparatus 100 according to the third embodiment. FIG. 14 illustrates the process procedure in a case where the extraction performance of a blood vessel wall of a coronary artery is used as an image index.

Step S301 in FIG. 14 is realized, for example, by invoking a program corresponding to the control function 37a from the memory circuitry 35 and executing the program by the processing circuitry 37. Step S302 is realized by reading out a corresponding program from the memory circuitry 35 and executing the program by the image reconstruction circuitry 36. Steps S303 and S307 are realized by invoking a program corresponding to the analysis function 37b from the memory circuitry 35 and executing the program by the processing circuitry 37. Steps S304, S305, and S310 are realized by invoking a program corresponding to the selection function 37c from the memory circuitry 35 and executing the program by the processing circuitry 37. Step S306 and S308 are realized by invoking a program corresponding to the presentation function 37e from the memory circuitry 35 and executing the program by the processing circuitry 37.

In the X-ray CT apparatus 100 according to the third embodiment, the processing circuitry 37 first collects pieces of projection data (Step S301). The image reconstruction circuitry 36 reconstructs volume data in each cardiac phase (Step S302). The processing circuitry 37 then extracts a blood vessel wall of a coronary artery respectively from the reconstructed pieces of volume data of the respective cardiac phases (Step S303). The processing circuitry 37 divides the cardiac phases 70% to 90% into a plurality of regions (Step S304), and selects a cardiac phase in each region (Step S305).

The processing circuitry 37 then determines whether the selected cardiac phase satisfies certain conditions (Step S306). If the selected cardiac phase satisfies the conditions (YES at Step S306), the processing circuitry 37 performs fluid analysis by using the volume data of the selected cardiac phase (Step S307).

On the other hand, if the selected cardiac phase does not satisfy the conditions (NO at Step S306), the processing circuitry 37 displays a warning (Step S308) and determines whether a reselection operation has been received (Step S309). If a reselection operation has been received (YES at Step S309), the processing circuitry 37 reselects a cardiac phase based on the conditions (Step S310). On the other hand, if a reselection operation has not been received (NO at Step S309), the processing circuitry 37 performs fluid analysis by using the volume data in the selected cardiac phases (Step S307).

Figure 15:
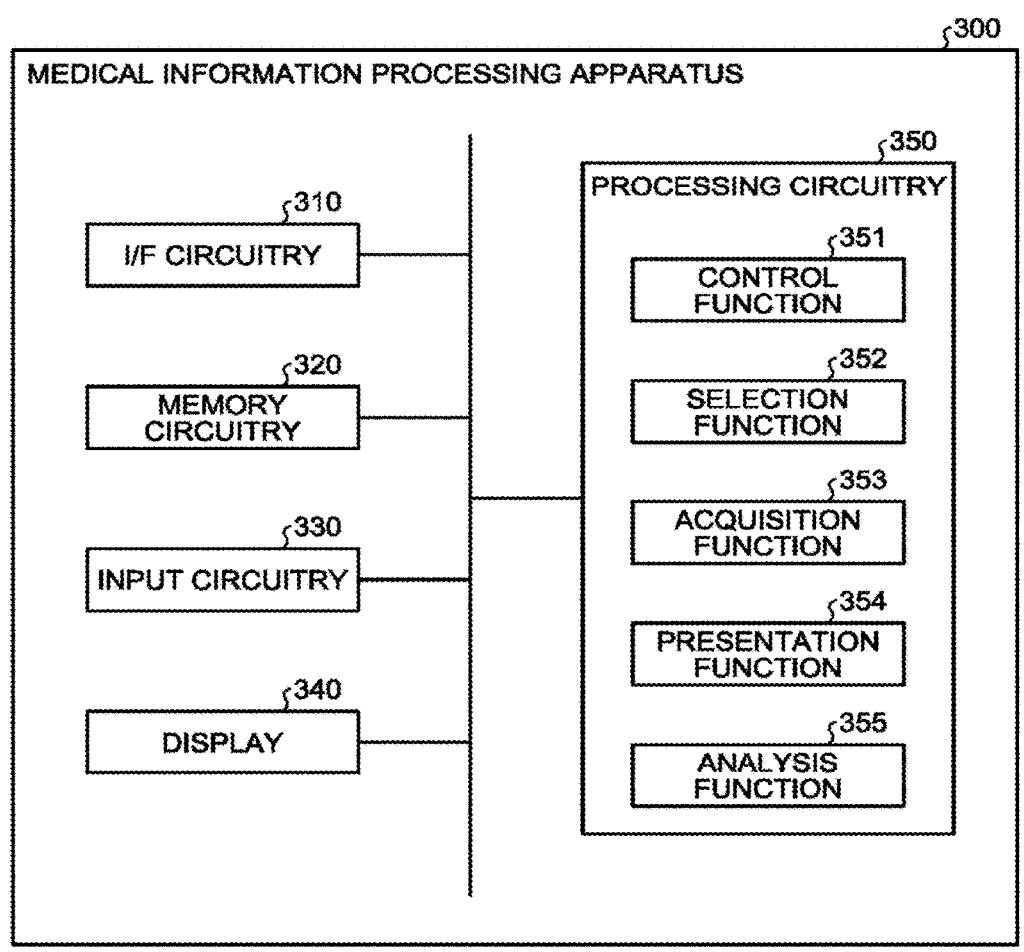
FIG. 15 a diagram illustrating an example of a configuration of a medical information processing apparatus according to the third embodiment.

In the embodiments described above, the case where the X-ray CT apparatus 100 performs various types of processing has been described. However, the embodiment is not limited thereto, and for example, various types of processing can be performed in the medical information processing apparatus 300. FIG. 15 is a diagram illustrating an example of a configuration of the medical information processing apparatus 300 according to the third embodiment.

For example, as illustrated in FIG. 15, the medical information processing apparatus 300 includes I/F (interface) circuitry 310, memory circuitry 320, input circuitry 330, a display 340, and processing circuitry 350.

The I/F circuitry 310 is connected to the processing circuitry 350 to control transmission and communication of various pieces of data performed between various types of X-ray CT apparatus 100 or image storage apparatus 200 connected via the network 400. For example, the I/F circuitry 310 is realized by a network card, a network adapter, an NIC (Network Interface Controller), or the like. In the third embodiment, the I/F circuitry 310 receives CT image data from the X-ray CT apparatus 100 or the image storage apparatus 200, and outputs the received CT image data to the processing circuitry 350.

The memory circuitry 320 is connected to the processing circuitry 350 and memorizes therein various types of data. For example, the memory circuitry 320 is realized by a semiconductor memory device such as a RAM (Random Access Memory) or a flash memory, a hard disk, an optical disk, or the like. In the third embodiment, the memory circuitry 320 memorizes therein CT image data received form the X-ray CT apparatus 100 or the image storage apparatus 200.

The input circuitry 330 is connected to the processing circuitry 350 and converts an input operation received from an operator to an electric signal to output the signal to the processing circuitry 350. The input circuitry 330 is realized by, for example, a trackball, a switch button, a mouse, a keyboard, or a touch panel.

The display 340 is connected to the processing circuitry 350 and displays thereon various pieces of information and various types of image data output from the processing circuitry 350. For example, the display 340 is realized by a liquid crystal monitor, a CRT (Cathode Ray Tube) monitor, a touch panel, or the like.

The processing circuitry 350 controls various constituent elements provided in the medical information processing apparatus 300 in response to an input operation received from an operator via the input circuitry 330. For example, the processing circuitry 350 is realized by a processor. In the third embodiment, the processing circuitry 350 causes the CT image data output from the I/F circuitry 310 to be memorized in the memory circuitry 320. The processing circuitry 350 reads cut the CT image data from the memory circuitry 320 and displays the CT image data on the display 340.

The processing circuitry 350 executes, as illustrated in FIG. 15, a control function 351, a selection function 352, an acquisition function 353, a presentation function 354, and an analysis function 355. The control function 351 controls the entire medical information processing apparatus 300. The selection function 352 performs identical processing as the selection function 37c described above. The acquisition function 353 performs identical processing as the acquisition function 37d described above. The presentation function 354 performs identical processing as the presentation function 37e described above. The analysis function 355 performs identical processing as the analysis function 37b described above.

In the embodiments described above, the case where the various processing functions are realized by a single processing circuitry (the processing circuitry 37 and the processing circuitry 350) has been described; however, the embodiment is not limited thereto. For example, the processing circuitry 37 and the processing circuitry 350 can be configured by combining a plurality of independent processors and realize the respective processing functions by executing the respective programs by the processors. Further the respective processing functions provided in the processing circuitry 37 and the processing circuitry 350 can be appropriately distributed to a plurality of processing circuits or integrated into a single processing circuit and realized.

The term "processor" used in the descriptions of the respective embodiments described above represents, for example, a CPU (Central Processing Unit), a GPU (Graphics Processing Unit), or a circuit such as an Application Specific Integrated Circuit (ASIC) or a programmable logic device (for example, a Simple Programmable Logic Device (SPLD), a Complex Programmable Logic Device (CPLD), and a Field Programmable Gate Array (FPGA)). In this example, instead of storing a program in a storage (memory) circuitry, it is possible to directly incorporate a program within a circuit of a processor. In this case, the processor realizes its functions by reading out and executing the program incorporated within the circuit of the processor. Further, the respective processors in the embodiments described above are not limited to those configured as a single circuit, and it is also possible to configure the processor as a single processor by combining a plurality of independent circuits and to realize its functions.

The program executed by a processor is incorporated in a ROM (Read Only Memory), a storage unit, or the like in advance and provided. The program can be provided while being recorded in a computer-readable storage medium such as a CD (Compact Disk)-ROM, an ED (Flexible Disk), a CD-R (Recordable), and a DVD (Digital Versatile Disk), as a file of an installable format or an executable format. Besides, the program can be stored in a computer connected to a network such as the Internet, and then provided or distributed by being downloaded via the network. For example, the program is constituted by modules including respective functional units. As actual hardware, while a CPU reads a program from a storage medium such as a ROM and executes the program, respective modules are loaded on a main storage device and are created on the main storage device.

According to at least one of the embodiments described above, appropriate data can be selected easily.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray CT apparatus comprising:
processing circuitry configured to
collect pieces of image data in a plurality of time phases that contain at least a part of a coronary artery of a heart;
acquire image indexes regarding a plurality of pieces of the image data;
extract a set of image data from combinations of pieces of image data having a larger time interval than a predetermined time interval, of the pieces of image data, based on the image indexes in the respective pieces of image data; and
perform fluid analysis regarding the coronary artery based on the extracted set of image data to obtain a fluid parameter regarding the coronary artery.

2. The X-ray CT apparatus according to claim 1, wherein the processing circuitry is configured to extract the set of image data from a time phase that is a Wave Free Period in a heartbeat time phase for one heartbeat.

3. The X-ray CT apparatus according to claim 1, wherein the processing circuitry is configured to extract the set of image data from a cardiac phase of 70% or after in a heartbeat time phase for one heartbeat.

4. The X-ray CT apparatus according to claim 1, wherein the processing circuitry is configured to extract a set of image data having an image quality index in the respective pieces of image data equal to or larger than a predetermined threshold from the combination of image data.

5. The X-ray CT apparatus according to claim 1, wherein the processing circuitry is configured to extract the set of image data from the combination of image data based on an extraction result of a predetermined portion included in the respective pieces of image data.

6. The X-ray CT apparatus according to claim 5, wherein the predetermined portion is a blood vessel wall of the coronary artery or a core line of the coronary artery.

7. The X-ray CT apparatus according to claim 1, wherein the processing circuitry is configured to evaluate movement with pulsation of the heart in the respective pieces of image data in time phases included in a Wave Free Period based on the image indexes, and extract a set of image data in a time phase in which movement with pulsation is relatively small.

8. The X-ray CT apparatus according to claim 7, wherein the processing circuitry is configured to evaluate the movement with pulsation based definition in a coronary artery region included in the image data.

9. The X-ray CT apparatus according to claim 7, wherein the processing circuitry is configured to divide the Wave Free Period into a plurality of partial ranges, and extract a set of image data corresponding to a time phase in which the movement with pulsation is relatively small from time phases included in the partial range, for each partial range.

10. The X-ray CT apparatus according to claim 9, wherein the processing circuitry is configured to divide the Wave Free Period into the partial ranges so that widths of the partial ranges approximate to each other.

11. The X-ray CT apparatus according to claim 7, wherein the processing circuitry is configured to extract at least image data corresponding to a time phase near an upper end and image a corresponding to a time phase near a lower end in the Wave Free Period, as the set of image data.

12. The X-ray CT apparatus according to claim 7, wherein the processing circuitry is configured to extract pieces of image data corresponding to the plurality of time phases so that a time interval between the time phases becomes equal to or larger than a predetermined threshold, in time phases included in the Wave Free Period.

13. The X-ray CT apparatus according to claim 1, wherein the processing circuitry is configured to extract the set of image data so that respective time intervals between adjacent time phases in the set of image data are large and approximate to each other.

14. The X-ray CT apparatus according to claim 1, wherein the processing circuitry is configured to extract the set of image data at a time of transfer of the image data.

15. The X-ray CT apparatus according to claim 1, wherein the processing circuitry is configured to extract the set of image data at a time of activation of an application of the fluid analysis.

16. The X-ray CT apparatus according to claim 1, wherein the processing circuitry is configured o present a warning to an operator, when the extracted set of image data does not comply with a predetermined condition.

17. A medical information processing apparatus comprising:
processing circuitry configured to
acquire image indexes regarding pieces of image data in a plurality of time phases that contain at least a part of a coronary artery of a heart;
extract a set of image data from combinations of pieces of image data having a larger time interval than a predetermined time interval, of the pieces of image data, based on the image indexes in the respective pieces of image data; and
perform fluid analysis regarding the coronary artery based on the extracted set of image data to obtain a fluid parameter regarding the coronary artery.

18. A medical information processing method comprising:
acquiring image indexes regarding pieces of image data in a plurality of time phases that contain at least a part of a coronary artery of a heart;
extracting a set of image data from combinations of pieces of image data having a larger time interval than a predetermined time interval, of the pieces of image data, based on the image indexes in the respective pieces of image data; and
performing fluid analysis regarding the coronary artery based on the extracted set of image data to obtain a fluid parameter regarding the coronary artery.

* * * * *